US012037363B2

(12) United States Patent
Roy et al.

(10) Patent No.: US 12,037,363 B2
(45) Date of Patent: *Jul. 16, 2024

(54) PEPTIDES FOR COVID-19 PREVENTION AND TREATMENT

(71) Applicant: SOTIRA COVID, LLC, Phoenix, AZ (US)

(72) Inventors: Avik Roy, Phoenix, AZ (US); Carl Gunnar Gottschalk, Phoenix, AZ (US)

(73) Assignee: SOTIRA COVID, LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/393,328

(22) Filed: Aug. 3, 2021

(65) Prior Publication Data

US 2022/0024988 A1 Jan. 27, 2022

Related U.S. Application Data

(63) Continuation of application No. 17/065,514, filed on Oct. 7, 2020, now Pat. No. 11,078,242.

(60) Provisional application No. 63/031,530, filed on May 28, 2020.

(51) Int. Cl.
*C07K 14/005* (2006.01)
*A61K 38/00* (2006.01)

(52) U.S. Cl.
CPC ............ *C07K 14/005* (2013.01); *A61K 38/00* (2013.01); *C12N 2770/20022* (2013.01); *C12N 2770/20033* (2013.01)

(58) Field of Classification Search
None
See application file for complete search history.

(56) References Cited

U.S. PATENT DOCUMENTS 11,129,892 B1 * 9/2021 Gilbert ................. A61K 39/145

OTHER PUBLICATIONS

Hou, Y., et al., 2010, Angiotensin-converting enzyme 2 (ACE2) proteins of different bat species confer variable susceptibility to SARS-CoV entry, Arch. Virol. 155:1563-1569. (Year: 2010).*
Gait and Karn, Tibtech vol. 13, pp. 430-438 (Year: 1995).*
Naider and Anglister (Current Opinion in Structural Biology vol. 19, pp. 473-482 (Year: 2009).*
Gali et al. ( Antimicrob Agents Chemother vol. 54, pp. 5105-5114 (Year: 2010).*
Chen et al., J of Virology vol. 87, pp. 10777-10783 (Year: 2013).*
Basle et al. (Chemistry & Biology vol. 17 pp. 213-227). (Year: 2010).*
Hoffmann et al. (Cell 181, 271-280 (Year: 2020).*

* cited by examiner

*Primary Examiner* — Shanon A. Foley
*Assistant Examiner* — Myron G Hill
(74) *Attorney, Agent, or Firm* — ENTRALTA PLLC; Peter D. Weinstein; James F. Fleming

(57) ABSTRACT

Embodiments include therapeutic peptides for preventing or reducing the transmission of a coronavirus such as SARS-CoV2. Also included are methods of using therapeutic peptides for reducing or preventing transmission of a coronavirus such as SARS-CoV2. The therapeutic peptides can prevent a region of the surface glycoprotein "spike" on SARS-CoV2 from interacting with angiotensin converting enzyme-2 (ACE-2) of host cells.

5 Claims, 10 Drawing Sheets

Specification includes a Sequence Listing.

Binding Complex of SARS-CoV1 and ACE-2

Binding of Complex of SARS-CoV S-glycoprotein and ACE-2

Inhibition of Binding Complex of SARS-CoV2
S-glycoprotein and ACE-2 with ACIS Peptide

FIG. 2C

BLItz assay Showing Affinity of ACIS Peptide Toward the ACE-2 Enzyme

BLItz assay Showing Maximum Affinity at 2.86 nM

Effect of ACIS on inhibiting the complex formation between ACE-2 and S-Glycoprotein Cytopathic Effect Test to Measure Infectivity of Residual Virus Present in the Supernatants of ACIS-treated VERO cells
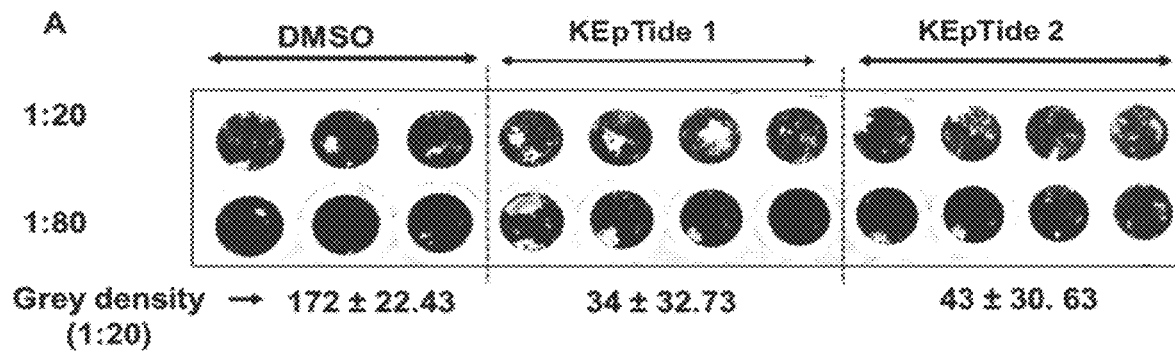
FIG. 5A
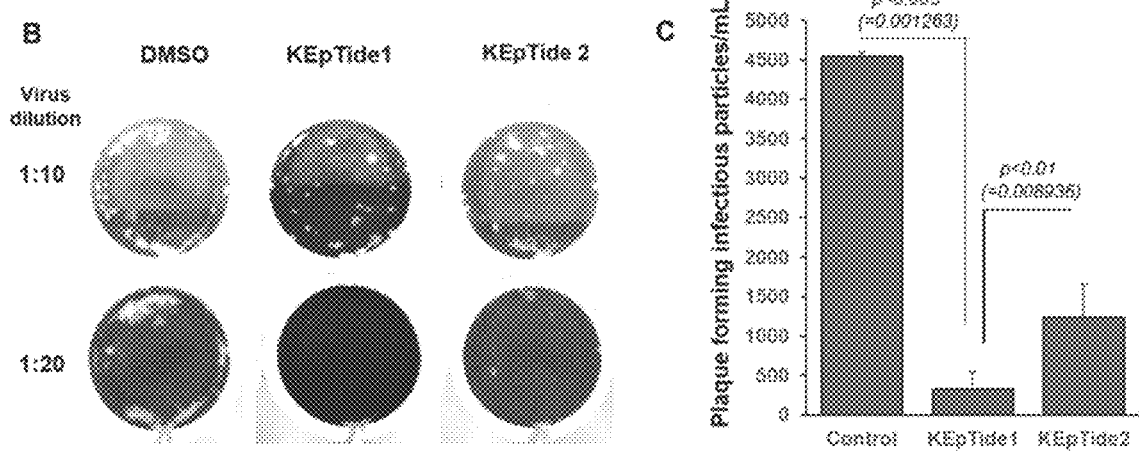
FIG. 5B
FIG. 5C Effect of KEPTIDE on the Attenuation of Acute Infection (2 hours) of SARS-CoV2 cells in VERO E6

Effect of KEPTIDE on the Attenuation of Chronic or Secondary Infection (6 hours) of SARS-CoV2 cells in VERO E6

- no DMSO
- DMSO
- ACIS [25 µM]
- Scrambled ACIS [25 µM]

Assessment of the Bioavailability of KEPTIDE1 in Lungs and Blood
FIG. 8A
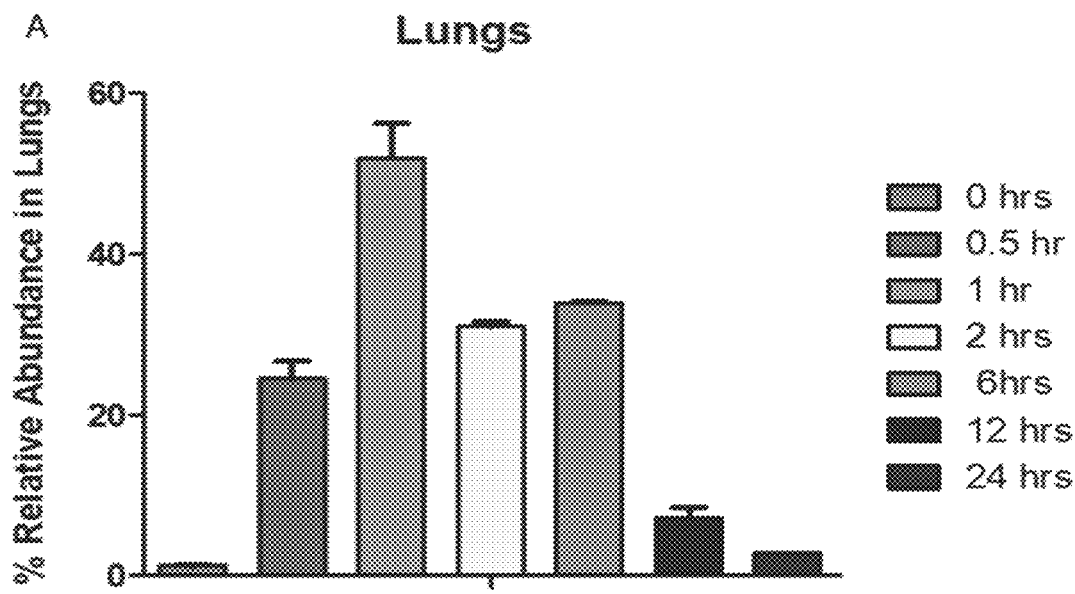
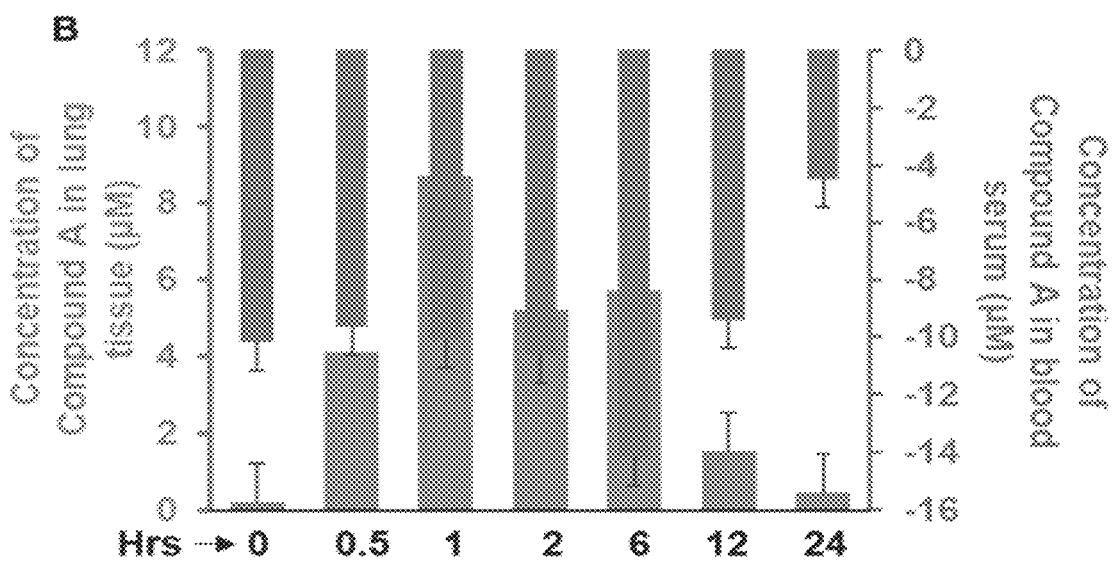
FIG. 8B Effect of Intranasally Administered KEPTIDE

SEQUENCE LISTING

<160> NUMBER OF SEQ ID NOS: 2

<210> SEQ ID NO 1
<211> LENGTH: 13
<212> TYPE: PRT
<213> ORGANISM: artificial
<220> FEATURE:
<223> OTHER INFORMATION: L(6-7) loop of SARS-CoV2 / ACIS Peptide

<400> SEQUENCE: 1

Phe Gln Pro Thr Asn Gly Val Gly Tyr Gln Pro Tyr Gly
1               5                   10

-continued

```
<210> SEQ ID NO 2
<211> LENGTH: 11
<212> TYPE: PRT
<213> ORGANISM: artificial
<220> FEATURE:
<223> OTHER INFORMATION: L(6-7) loop of SARS-CoV1

<400> SEQUENCE: 2

Phe Tyr Thr Thr Thr Gly Ile Gly Tyr Gln Pro
1               5                   10
```

PEPTIDES FOR COVID-19 PREVENTION AND TREATMENT

RELATED APPLICATIONS

This application is a Continuation Application of U.S. patent Ser. No. 17/065,514 and claims priority to U.S. Provisional Patent Application No. 63/031,530 filed on May 28, 2020. The contents of the aforementioned application are incorporated herein by reference.

FIELD OF THE INVENTION

The invention relates to chemically modified peptides with therapeutic uses, specifically, it relates to a peptide that can block the interaction of surface glycoprotein on SARS-CoV2 with angiotensin converting enzyme-2 (ACE-2) of host cells.

BACKGROUND

A pandemic is an epidemic of disease that has spread across a large region, such as multiple continents, that affects a substantial number of people. There a several pandemics that have been documented throughout human history, such as smallpox and tuberculosis. The most fatal pandemic in recorded history was the Black Death (also known as The Plague), which killed an estimated 75-200 million people in the 14th century. Other notable pandemics include the 1918 influenza pandemic (Spanish flu) and the recent Covid-19 pandemic.

The basic strategies to control of an outbreak include containment and mitigation. Containment generally includes contact tracing and isolating infected individuals to stop the disease from spreading. Mitigation is employed when it is no longer possible to contain the spread of the disease. In this stage, additional measures are taken to try to slow the spread of the disease and mitigate its effects on society and the healthcare system.

Managing an infectious disease outbreak can include efforts to decrease the epidemic peak, known as "flattening the curve." This helps decrease the risk of health services being overwhelmed and provides more time for the development of vaccines and/or treatments. Interventions may be taken to manage the outbreak including: personal preventive measures such as hand hygiene, wearing face-masks, and self-quarantine; community measures aimed at social distancing such as closing schools and cancelling mass gatherings; community engagement to encourage acceptance and participation in such interventions; and environmental measures such as cleaning of surfaces.

Another strategy, suppression, requires more extreme long-term non-pharmaceutical interventions by attempting to reduce the basic reproduction number to less than one. The suppression strategy, which includes stringent population-wide social distancing, home isolation of cases, and household quarantine, was undertaken by communities during the COVID-19 pandemic. Entire cities were placed under lockdown which presented considerable social and economic costs. Because these strategies have limitations and high costs, treatments and immunizations are the needed to respond to pandemic diseases.

Coronaviruses (CoV) are a large family of viruses that cause illness ranging from the common cold to more severe diseases such as Middle East Respiratory Syndrome (MERS-CoV) and Severe Acute Respiratory Syndrome (SARS-CoV). A new strain of coronavirus (SARS-CoV-2) causes Coronavirus disease 2019, or Covid-19, which was declared a pandemic by the WHO on 11 Mar. 2020. Common signs of Covid-19 infection include respiratory symptoms, fever, cough, shortness of breath, and breathing difficulties. In more severe cases, infection can cause pneumonia, severe acute respiratory syndrome, kidney failure and death.

Because of the novelty of Covid-19, federal, state and local authorities took extreme efforts to contain and mitigate the infections. Economies suffered as unemployment increased to record numbers. Authorities struggled with efforts to salvage economies while containing infections. Businesses gradually began to open with social distancing efforts. Scientists and health care professionals faced pressure to quickly develop effective treatments and immunizations to respond to Covid-19.

Groups in several countries have worked aggressively to develop a Covid-19 vaccine to provide acquired immunity. As of the date of this paper, no vaccine candidate has completed clinical trials to prove its safety and efficacy. A vaccine for an infectious disease has never been produced in less than several years, and no vaccine exists for preventing a coronavirus infection in humans. Further, there are several unknowns related to a Covid-19 vaccine. For example, it is unknown how long immunity will last. With seasonal human coronaviruses, immunity can last anywhere from 80 days to a few years, and studies are showing different lengths of time. As a result, it is uncertain what the true durability of a vaccine will be. For this reason, alternative treatments and therapies are needed.

A study performed by Goutret et. al found that the repurposing of anti-malaria drug hydroxychloroquine (HCQ) attenuated viral load in Covid-19 patients and this beneficial effect was further enhanced in combination with macrolide anti-bacterial drug such as azithromycin (AZT) (Gautret, et. al (2020) Hydroxychloroquine and azithromycin as a treatment of Covid-19: results of an open-label non-randomized clinical trial. Int J Antimicrob Agents, 105949). However, the trial of Goutret and colleagues did not provide sufficient evidence to support wide-scale application of HCQ treatment for the treatment of Covid-19, mainly due to the lack of rigorous methodology, cohort procedure and analysis. Moreover, HCQ treatment itself has several adverse side-effects including severe abdominal pain, fatigue, depression, hair loss, irregular heartbeat, and cardiac failure. In combination with strong antibiotic like AZT, HCQ could impose severe comorbidity. Moreover, in response to non-specific action of HCQ, there is a risk for the generation of HCQ-resistant strain of coronavirus that might impose even a greater threat. Repurposing of other anti-retroviral drugs such as Ebola drug remedesivir and HIV drugs including lopinavir and ritonavir have been reported to display protective effects against Covid-19. However, these drugs are associated with severe side effects in Covid-19 patients such as respiratory failure, depigmentation of skin and anemia. With these considerations, the current pandemic demands a specific therapeutic strategy without deleterious effects.

Accordingly, there is a need for a means of preventing and/or treating coronaviruses infections. Embodiments of the invention include therapeutic peptides for preventing or attenuating the transmission of a coronavirus such as SARS-CoV2

SUMMARY OF THE INVENTION

The inventions described and claimed herein have many attributes and embodiments including, but not limited to, those set forth or described or referenced in this brief summary. The inventions described and claimed herein are not limited to, or by, the features or embodiments identified in this summary, which is included for purposes of illustration only and not restriction.

Applicants present a peptide that prevents the interaction of surface glycoprotein (S-glycoprotein) of coronavirus particles with angiotensin converting enzyme-2 (ACE-2) of host cells. Applicants have identified a loop ($L_{6\rightarrow7}$) between β6 and β7 strands of S-glycoprotein that intimately engages multiple hydrogen-bond (H-bond) interactions with ACE-2 enzyme. Accordingly, an embodiment is a tridecapeptide "ACIS" (ACE-2 Interacting motif of S-glycoprotein) that binds to the $L_{6\rightarrow7}$ loop of SARS-CoV2. Another embodiment is a method of preventing or "neutralizing" the interaction of a coronavirus with ACE-2 of a host cell using a therapeutic peptide (i.e. ACIS).

One embodiment is a therapeutic peptide that can decreases the transmissibility or average basic reproduction number ($R_0$) of a virus such as a coronavirus. Another embodiment is a therapeutic peptide of sequence FQPTNGVGYQPYG (SEQ ID NO: 1) (i.e., ACIS peptide or KEPTIDE COVID™).

One embodiment is a polynucleotide encoding a peptide of sequence FQPTNGVGYQPYG (SEQ ID NO: 1). Another embodiment is an expression vector that includes this polynucleotide. Yet another embodiment is a host cell transfected with the vector and a method of producing a therapeutic peptide of sequence FQPTNGVGYQPYG (SEQ ID NO: 1).

One embodiment is a C-terminal tag of lysine residue to augment the basic property to the peptide. Addition of lysine increases the isoelectric pH of the peptide, so that acid-loving exoproteases of SARS-CoV2 cannot digest and eliminate the peptide from the system. In addition to that, addition of lysine is required for the chemical modification of peptide with biotin (Vitamin H or B7) or any thienoimidazole derivative. The addition of a biotin molecule on the epsilon amino group of lysine is significant. The addition of biotin not only neutralizes the negative charge of carboxy terminal group, but also an electron exchange reaction on the diamino carbonyl group of biotin offers extra positive charge to the peptide. During testing, the biotin-modified KEPTIDE COVID was designated as KEPTIDE1.

One embodiment is the amidation of the free carboxylic acid group of C-terminal lysine residue. With that amidation, the negative C-terminal end of KEPTIDE1 is completely neutralized making it further resistant against all SARS CoV2 proteases. In addition, such embodiment facilitates the unipolarity in the peptide, neutralizes the carboxy terminal negative charge, prevents cyclic deactivation, and increases the affinity of KEPTIDE1 to the ACE-2 receptor.

One embodiment is a nasal spray or inhalant that includes a therapeutic peptide to treat a virus infection in a patient, such as a coronavirus infection. Another embodiment is a nasal spray or inhalant that includes a therapeutic peptide to decreases the transmissibility or average basic reproduction number ($R_0$) of a virus such as a coronavirus.

One embodiment is a method of using a therapeutic peptide to prevent or reduce the likelihood of infection from a virus such as a coronavirus. Another embodiment is a method of using a therapeutic peptide to decrease the transmissibility or average basic reproduction number ($R_0$) of a virus such as a coronavirus.

One embodiment is a method of using a therapeutic peptide to treat a virus infection in a patient, such as a coronavirus infection. One embodiment is an immunization that includes a peptide of sequence FQPTNGVGYQPYG (SEQ ID NO: 1) (i.e., ACIS peptide or KEPTIDE COVID) with the epsilon amino acid residue conjugated with biotin and the amidation of the carboxyl terminus on the C-terminal of the polypetide.

One embodiment is a method of preventing a virus infection comprising steps of (a) providing a patient that is susceptible to infection by a virus, (b) administering a therapeutic peptide to the respiratory system of the patient, and (c) monitoring the patient for signs/symptoms of the virus. The therapeutic peptide can have the amino acid sequence of SEQ ID NO: 1. Alternatively, one or more amino acids can be substituted such that the substitutions are conservative and the specificity of the peptide is not adversely affected. In this regard, the peptide can have at least 70%, at least 75%, at least 80%, at least 85%, at least 90% or at least 95% sequence identity to SEQ ID NO: 1.

One embodiment is a method of preventing a virus infection comprising steps of (a) identifying the formation of a complex between the virus and a host cell, (b) characterizing a chemical interaction between a surface protein on the virus and a receptor on the host cell, (c) identifying a protein sequence involved in the interaction, (d) producing a therapeutic peptide having at least 90% sequence identity to the protein sequence and (e) administering the therapeutic peptide to a patient to prevent formation of the complex between the virus and the host cell. The virus can be a coronavirus such as SARS-CoV2. The therapeutic peptide can be administered as a nasal spray or inhalant.

Another embodiment is a method of immunizing a patient against a coronavirus. The method can include exposing the patient to a peptide of SEQ ID NO: 1 so that the patient exhibits an immune response to the peptide. Yet another embodiment is a peptide capable of specifically binding to viral surface protein of a coronavirus and having neutralizing activity. The peptide can have the amino acid sequence of SEQ ID NO. 1 and one or more conservative amino acid substitutions.

In still another aspect, the present specification provides a use of the therapeutic protein or the pharmaceutical composition including the same in the preparation of drugs for the prevention or treatment of a viral infection.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIG. 2C depicts ACIS peptide (red) which inhibits the interaction between SARS-CoV2 S-glycoprotein (yellow) and ACE-2 (blue). The arrows depict the displacement of S-glycoprotein far from ACE-2 enzyme.

FIG. 5A shows Cytopathic Effect Test to measure infectivity of residual virus present in the supernatants of ACIS-treated VERO cells.

FIGS. 5B and 5C show the effect of KEPTIDEs on SARS-CoV2 infectivity by plaque assay FIGS. 6A and 6B show effect of KEPTIDE on the attenuation of acute infection (2 hours) of SARS-CoV2 cells in VERO E6.

FIGS. 7A and 7B show the effect of KEPTIDE on the attenuation of chronic or secondary infection (6 hours) of SARS-CoV2 cells in VERO E6.

FIGS. 8A and 8B show assessment of the bioavailability of KEPTIDE1 in lungs and blood.

FIGS. 9A, 9B, 9C, and 9D show the effect of intranasally administered KEPTIDE COVID on the health of the subject, specifically as to its body weight (FIG. 9A), body temperature (FIG. 9B), heart rate (FIG. 9C), and oxygen saturation (FIG. 9D).

DEFINITIONS

Reference in this specification to "one embodiment/aspect" or "an embodiment/aspect" means that a particular feature, structure, or characteristic described in connection with the embodiment/aspect is included in at least one embodiment/aspect of the disclosure. The use of the phrase "in one embodiment/aspect" or "in another embodiment/aspect" in various places in the specification are not necessarily all referring to the same embodiment/aspect, nor are separate or alternative embodiments/aspects mutually exclusive of other embodiments/aspects. Moreover, various features are described which may be exhibited by some embodiments/aspects and not by others. Similarly, various requirements are described which may be requirements for some embodiments/aspects but not other embodiments/aspects. Embodiment and aspect can be in certain instances be used interchangeably.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

As applicable, the terms "about" or "generally", as used herein in the specification and appended claims, and unless otherwise indicated, means a margin of +/−20%. Also, as applicable, the term "substantially" as used herein in the specification and appended claims, unless otherwise indicated, means a margin of +/−10%. It is to be appreciated that not all uses of the above terms are quantifiable such that the referenced ranges can be applied.

The term "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed. An active agent can be a primary active agent, or in other words, the component(s) of a composition to which the whole or part of the effect of the composition is attributed. An active agent can be a secondary agent, or in other words, the component(s) of a composition to which an additional part and/or other effect of the composition is attributed.

A "pharmaceutical composition" can include the combination of an active agent, such as a therapeutic peptide, with a carrier, inert or active, in a sterile composition suitable for diagnostic or therapeutic use in vitro, in vivo or ex vivo.

The term "average basic reproduction number" or "$R_0$" refers to an epidemiologic metric that describes the transmissibility of infectious agents. $R_0$ measures the expected number of secondary infections produced by a single infectious individual in a susceptible population during the mean infectious period.

The term "coronavirus" refers to a group of related RNA viruses that cause diseases in mammals and birds. In humans, these viruses cause respiratory tract infections that can range from mild to lethal. Mild illnesses include some cases of the common cold (which is caused also by certain other viruses, predominantly rhinoviruses), while more lethal varieties can cause SARS, MERS, and COVID-19. There are presently no vaccines or antiviral drugs to prevent or treat human coronavirus infections.

The term "SARS" or "severe acute respiratory syndrome" refers to a viral respiratory disease of zoonotic origin that surfaced in the early 2000s caused by severe acute respiratory syndrome coronavirus (SARS-CoV or SARS-CoV-1), the first-identified strain of the SARS coronavirus species severe acute respiratory syndrome-related coronavirus (SARSr-CoV). The syndrome caused the 2002-2004 SARS outbreak. In 2019, its successor, the related virus strain Severe Acute Respiratory Syndrome Coronavirus 2 (SARS-CoV-2), was discovered.

The term "Covid-19" or "Coronavirus disease 2019" refers to a severe acute respiratory syndrome (SARS) caused by a virus known as SARS-Coronavirus 2 (SARS-CoV2).

The term "angiotensin converting enzyme-2," "ACE2" or "ACE-2" refers to an enzyme attached to the outer surface (cell membranes) of cells in the lungs, arteries, heart, kidney,

Figure 1:
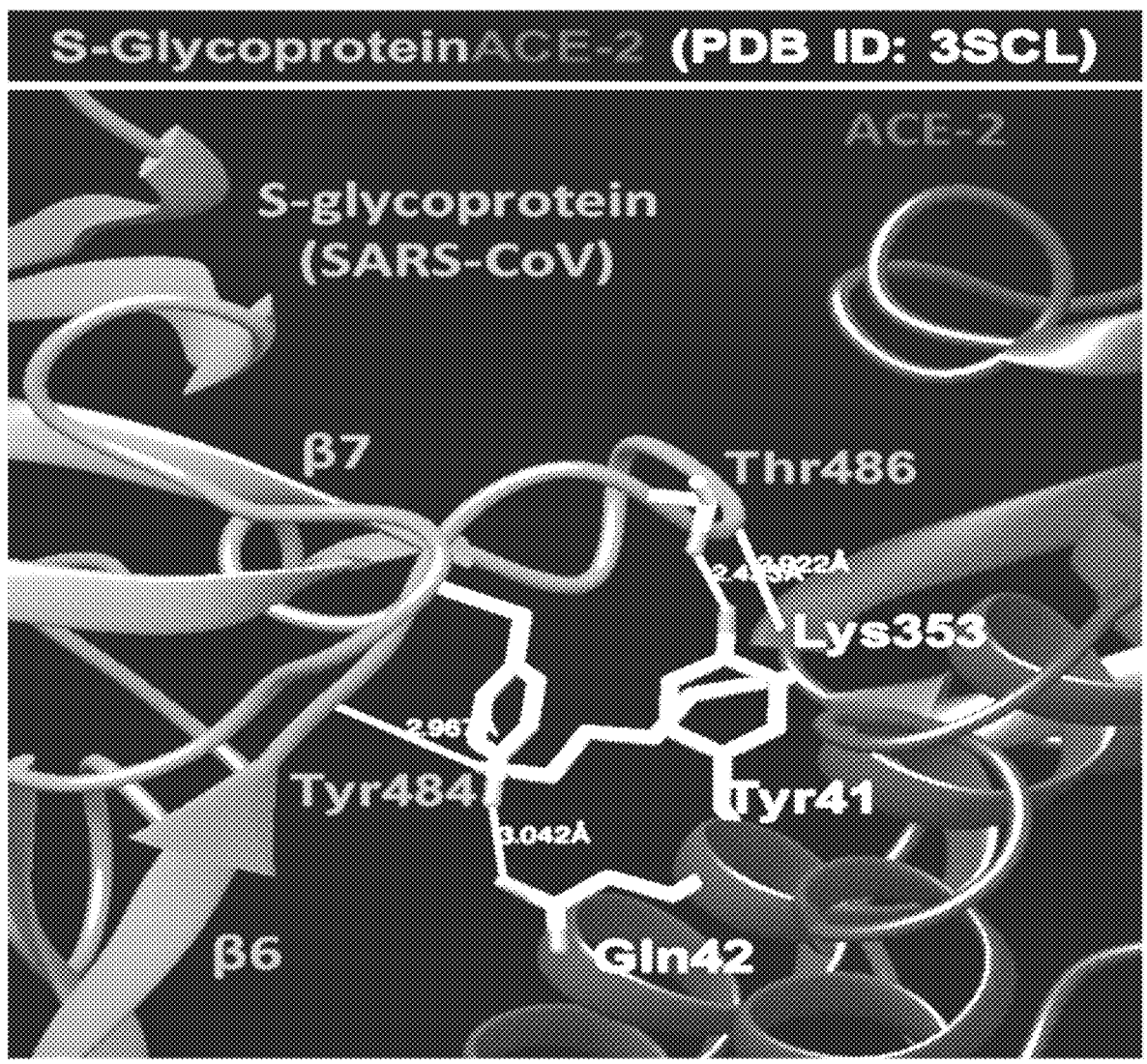
FIG. 1 depicts the three-dimensional binding complex of SARS-CoV1 and ACE-2.

and intestines. ACE2 lowers blood pressure by catalyzing the hydrolysis of angiotensin II (a vasoconstrictor peptide) into angiotensin (a vasodilator). ACE2 counters the activity of the related angiotensin-converting enzyme (ACE) by reducing the amount of angiotensin-II and increasing Ang making it a promising drug target for treating cardiovascular diseases. ACE2 also serves as the entry point into cells for some coronaviruses including SARS-CoV-2. The human version of the enzyme is often referred to as hACE2.

The term "ACIS" or "ACE-2 Interacting motif of (S) glycoprotein" refers to the spike envelope glycoprotein on a SARS coronavirus particle. The entry of the SARS coronavirus (SCV) into cells is initiated by binding of its spike envelope glycoprotein (S) to a receptor, ACE-2 (human angiotensin converting enzyme 2 or "hACE2").

The term "LALIGN pairwise-alignment" refers to a method used to identify regions of similarity that may indicate functional, structural and/or evolutionary relationships between two biological sequences (protein or nucleic acid).

The term "PyDock rigid-body structural analysis" refers to a method of predicting protein-protein complex structures using FFT-based algorithms. It allows structural prediction of protein-protein interactions (PPIs).

The term "BLItz label-free bio-layer interferometry assay" refers to the use of a BLITZ System for Bio-layer interferometry (BLI), a label-free technology for measuring biomolecular interactions. It is an optical analytical technique that analyzes the interference pattern of white light reflected from two surfaces: a layer of immobilized protein on the biosensor tip, and an internal reference layer. Any change in the number of molecules bound to the biosensor tip causes a shift in the interference pattern that can be measured in real-time.

The term "fluorescein isothiocyanate" or "FITC" refers to a derivative of fluorescein used in various laboratory applications. FITC is reactive towards nucleophiles including amine and sulfhydryl groups on proteins.

The term "thienoimidazole derivative" refers to a heterocyclic compound with two five-carbon rings. One five-carbon ring is known as thiophene with molecular formula $C_4H_4S$ and another five-carbon ring is imidazole with formula $C_3H_4N_2$. A common example of thienoimidazole compound is biotin.

The term "$IC_{50}$" or "$IC_{50}$ value" refers to the concentration of a drug that reduces the activity (or binding) of another drug to an enzyme by 50%. Under certain conditions it can used to express the affinity of the enzyme inhibitor.

The term "vaccine" refers to a biological preparation that provides active acquired immunity to a particular infectious disease such as Covid-19. A vaccine typically contains an agent that resembles a disease-causing microorganism and is often made from weakened or killed forms of the microbe, its toxins, or one of its surface proteins. The agent stimulates the body's immune system to recognize the agent as a threat, destroy it, and to further recognize and destroy any of the microorganisms associated with that agent that it may encounter in the future.

The term "peptide vaccine" refers to a peptide that serves to immunize an organism against a pathogen. Peptide vaccines are often synthetic vaccines and mimic naturally occurring proteins from pathogens.

The term "X-ray crystallography" refers to the experimental science determining the atomic and molecular structure of a crystal, in which the crystalline structure causes a beam of incident X-rays to diffract into many specific directions. By measuring the angles and intensities of these diffracted beams, a crystallographer can produce a three-dimensional picture of the density of electrons within the crystal. From this electron density, the mean positions of the atoms in the crystal can be determined, as well as their chemical bonds, their crystallographic disorder, and various other information.

The term "subject" or "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "viral load," "viral burden" or "viral titer" refers to a numerical expression of the quantity of virus in a given volume of body fluid, usually blood plasma. It is often expressed as viral particles, or infectious particles per mL depending on the type of assay. A higher viral burden, titer, or viral load often correlates with the severity of an active viral infection.

As used herein, the term "recombinant" refers to polypeptides or polynucleotides that do not exist naturally and which may be created by combining polynucleotides or polypeptides in arrangements that would not normally occur together. The term can refer to a polypeptide produced through a biological host, selected from a mammalian expression system, an insect cell expression system, a yeast expression system, and a bacterial expression system.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity, neurodegeneration or pathological inflammation, normal human cells or tissues.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For example, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99% or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The term "variant" as used herein includes modifications or chemical equivalents of the amino acid and nucleotide sequences disclosed herein that perform substantially the same function as the proteins or nucleic acid molecules disclosed herein in substantially the same way. For example, variants of proteins disclosed herein include, without limitation, conservative amino acid substitutions. Variants of proteins disclosed herein also include additions and deletions to the proteins disclosed herein. In addition, variant peptides and variant nucleotide sequences include analogs and chemical derivatives thereof.

The present therapeutic peptide can have amino acid additions, deletions, or substitutions. A modified amino acid sequence is a sequence that is different from the native amino acid sequence due to a deletion, an insertion, a non-conservative or conservative substitution or combinations thereof of one or more amino acid residues. In one embodiment, the modification is a point mutation. In one aspect, the modified therapeutic peptide does not have a naturally occurring sequence.

The amino acid substitutions may be conservative or non-conservative. A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The most commonly occurring exchanges are Ala/Ser, Val/Ile, Asp/Glu, Thr/Ser, Ala/Gly, Ala/Thr, Ser/Asn, Ala/Val, Ser/Gly, Ala/Pro, Lys/Arg, Asp/Asn, Leu/Ile, Leu/Val, Ala/Glu and Asp/Gly, in both directions. Amino acid exchanges in proteins and peptides, which do not generally alter the activity of the proteins or peptides, are known in the art (H. Neurath, R. L. Hill, The Proteins, Academic Press, New York, 1979).

The term "derivative of a peptide" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

In one embodiment, a modified therapeutic peptide disclosed herein can have 1-13 amino acid additions, deletions, or substitutions. In one aspect, the therapeutic peptide has at least 1, at least 2, at least 3, at least 4, at least 5, at least 6, at least 7, at least 8, at least 9, at least 10, at least 11, at least 12 or at least 13 amino acid additions, substitutions, or deletions. Substitutions can be conservative or non-conservative. In another aspect, the therapeutic peptide can have at most 13, at most 12, at most 11, at most 10, at most 9, at most 8, at most 7, at most 6, at most 5, at most 4, at most 3, at most 2, or at most 1 amino acid additions, substitutions, or deletions. In yet another aspect, the therapeutic peptide can have 1-13, 1-12, 1-10, 1-9, 1-8, 1-7, 1-6, 1-5, 1-4, 1-3, 1-2, 2-4, 2-13, 2-12, 2-10, 2-9, 2-8, 2-7, 2-6, 2-5, 2-4, 2-3, 3-4, 3-13, 3-12, 3-10, 3-9, 3-8, 3-7, 3-6, 3-5, 3-4, 4-12, 4-10, 4-9, 4-8, 4-7, 4-6, 4-5, 5-12, 5-10, 5-9, 5-8, 5-7, 5-6, 5-5, 6-12, 6-10, 6-9, 6-8, 6-7, 7-13, 7-12, 7-10, 7-9, 7-8, 8-13, 8-12, 8-10, 8-9, 9-13, 9-12, 9-10, 10-12, 11-13, 11-12 or 12-13 amino acid additions, substitutions or deletions.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, m RNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher et al., *J. Biol. Chem.* 273(52):35095-35101 (1998).

As used herein, the term "prevention" means all of the actions by which the occurrence of the disease is restrained or retarded.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

The term "administration" refers to the introduction of an amount of a predetermined substance into a patient by a certain suitable method. The composition disclosed herein may be administered via any of the common routes, as long as it is able to reach a desired tissue, for example, but is not limited to, inhaling, intraperitoneal, intravenous, intramuscular, subcutaneous, intradermal, oral, topical, intranasal, intrapulmonary, or intrarectal administration. However, since peptides are digested upon oral administration, active ingredients of a composition for oral administration should be coated or formulated for protection against degradation in the stomach.

The term "subject" refers to those who a susceptible to infection or who are suspected of having or diagnosed with an infectious disease. However, any subject to be treated with the pharmaceutical composition disclosed herein is included without limitation. The pharmaceutical composition including the peptide disclosed herein is administered to a subject to prevent and/or treat viral infection.

Construction of suitable vectors containing the desired sequences and control sequences employs standard ligation and restriction techniques, which are well understood in the art (see Maniatis et al., in *Molecular Cloning: A Laboratory Manual*, Cold Spring Harbor Laboratory, New York (1982)). Isolated plasmids, DNA sequences, or synthesized oligonucleotides are cleaved, tailored, and re-ligated in the form desired.

All numerical designations, e.g., pH, temperature, time, concentration, and molecular weight, including ranges, are to be understood as approximations in accordance with common practice in the art. When used herein, the term "about" may connote variation (+) or (−) 1%, 5% or 10% of the stated amount, as appropriate given the context. It is to be understood, although not always explicitly stated, that the reagents described herein are merely exemplary and that equivalents of such are known in the art.

Many known and useful compounds and the like can be found in Remington's Pharmaceutical Sciences (13th Ed), Mack Publishing Company, Easton, PA—a standard reference for various types of administration. As used herein, the term "formulation(s)" means a combination of at least one active ingredient with one or more other ingredient, also commonly referred to as excipients, which may be independently active or inactive. The term "formulation" may or may not refer to a pharmaceutically acceptable composition for administration to humans or animals and may include compositions that are useful intermediates for storage or research purposes.

Other technical terms used herein have their ordinary meaning in the art that they are used, as exemplified by a variety of technical dictionaries. The particular values and configurations discussed in these non-limiting examples can be varied and are cited merely to illustrate at least one embodiment and are not intended to limit the scope thereof.

DESCRIPTION OF EMBODIMENTS

It is to be understood that both the foregoing general description and the following detailed description are exemplary and explanatory and are intended to provide further explanation of the subject technology as claimed. Additional features and advantages of the subject technology are set forth in the description below, and in part will be apparent from the description, or may be learned by practice of the subject technology. The advantages of the subject technology will be realized and attained by the structure particularly pointed out in the written description and claims hereof.

Recent studies have demonstrated that SARS-CoV2 employs its membrane-bound "S-glycoprotein" to interact with the host receptor ACE-2. This interaction plays a critical role in the entry of viral particles in human cells. However, the molecular details of that complex formation were not properly understood. Applicants have analyzed the complex formation of ACE-2 and S-glycoprotein of original Coronavirus-1 (SARS-CoV1) and determined that structural similarities permit development of therapies to treat Covid-19.

Previous studies have used X-ray diffraction to characterize the three-dimensional structure of S-glycoprotein of SARS-CoV1 and ACE-2 at a resolution of 3 Å. FIG. 1 depicts the three-dimensional structure formed by the interaction (i.e. complex) of SARS-CoV1 and ACE-2. SARS-CoV1 is depicted with the left ribbon and ACE-2 with the right ribbon. Table 1 presents a summary of the hydrogen bonding interactions.

TABLE 1

| H-Bond Interactions of SARS-CoV1 and ACE-2 | | |
|---|---|---|
| Donor | Acceptor | Distance (Å) |
| THR 31.A OG1 | TYR 442.E OH | 3.048 |
| THR 41.A OH | THR 486.E OG1 | 2.433 |
| THR 42.A NE2 | TYR 484.E OH | 3.042 |
| THR 353.A NZ | GLY 482.E O | 2.967 |
| THR 426.E NH2 | GLU 329.A OE1 | 3.143 |
| THR 436.E OH | FLU 38.A OE1 | 2.925 |
| THR 442.E OH | THR 31.A OG1 | 3.048 |
| THR 486.E OG1 | TYR 41.A Oh | 2.433 |
| THR 488.E N | LYS 353.A O | 2.922 |

Table 1 provides a summary of H-bonds that form between S-glycoprotein (identified as E unit) and ACE-2 protein (identified as A unit). According to the structural hallmarks, a single subunit of S-glycoprotein interacts with ACE-2 via a loop ($L_{6 \to 7}$) between its β6 and β7 strands. Applicants propose that a peptide of 11 amino acids with sequence of $^{483}$FYTTTGIGYQP$^{493}$ harboring TTGIGY sequence in the core located at $L_{6 \to 7}$ loop of S-glycoprotein is critical for the interaction of SARS-CoV1 with ACE-2 enzyme of host cell.

However, actual complex formation of S-glycoprotein and ACE-2 is complicated due to a large heterotrimeric assembly of S-glycoprotein on the surface of ACE-2 enzyme. Due to that large and complicated structural assembly, the overall complex of S-glycoprotein and ACE-2 has been difficult to resolve. A recent study provided further details of the interaction using Cryo-EM structural analysis. It revealed that S3 subunit of the heterotrimeric S-glycoprotein of SARS-CoV1 indeed employed its $L_{6 \to 7}$ loop for its interaction with ACE-2 (Song et. al (2018) Cryo-EM structure of the SARS coronavirus spike glycoprotein in complex with its host cell receptor ACE2. PLoS pathogens 14, e1007236). However, it was not clear if SARS-CoV2 exhibits similar interaction with ACE-2 enzyme.

Applicants have found that S-glycoprotein of SARS-CoV2 shares a significant sequence homology with that of SARS-CoV1. Based on LALIGN pairwise-alignment study, SARS-CoV2 displays 92% sequence homology with Coronavirus-1 in S-glycoprotein. However, $L_{6 \to 7}$ loop of SARS-CoV2 is constituted with a tridecapeptide $^{497}$FQPTNGVGYQPYG$^{509}$. To understand the structural significance of this $L_{6 \to 7}$ loop, Applicants performed a homology modeling study to analyze the complex formation between SARSCoV2 S-glycoprotein and ACE-2.

Figure 2A:
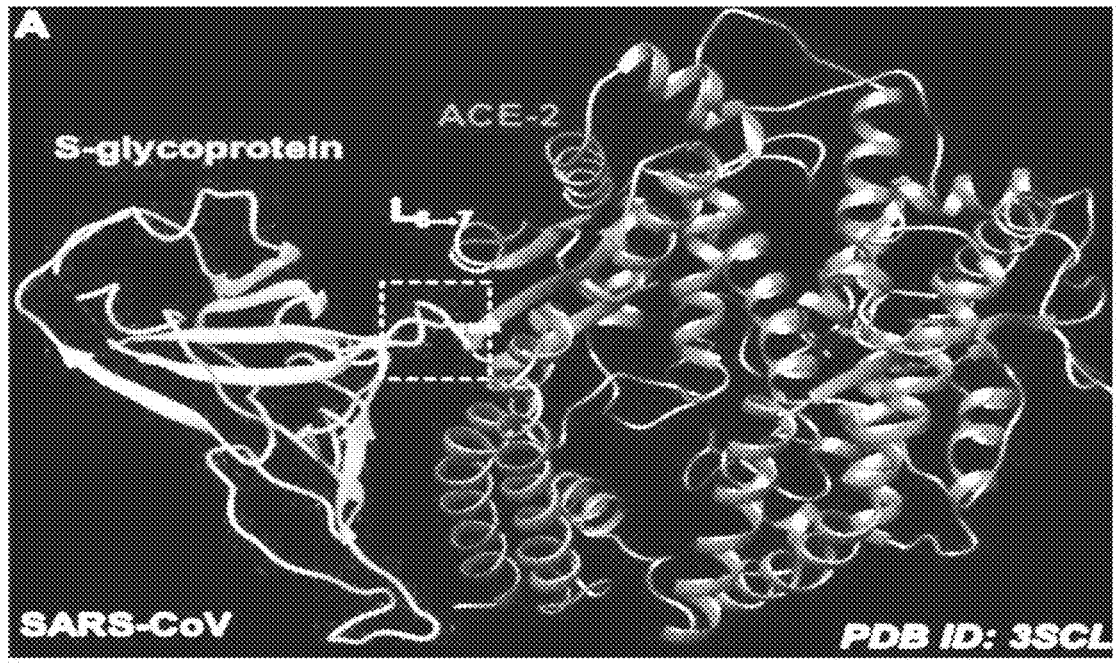
FIG. 2A depicts SARS-CoV S-glycoprotein bound to ACE-2.
Figure 2B:
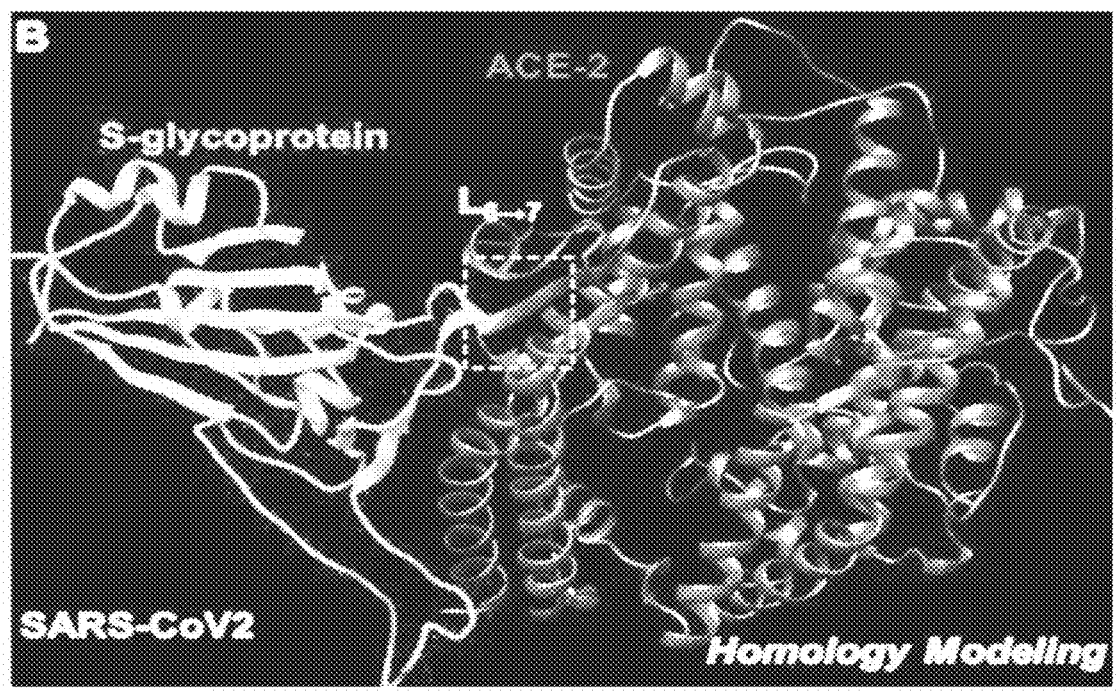
FIG. 2B is a simulated structure of SARSCoV2 glycoprotein that shows similar structure with $L_{6\rightarrow7}$ loop interacting with ACE-2.

Interestingly, Applicants observed a similar loop formation with SARS-CoV2 peptide in the interface of ACE-2 protein. FIG. 2A depicts the three-dimensional structure formed by the interaction of SARS-CoV1 S-glycoprotein and ACE-2. SARS-CoV1 is depicted with the left ribbon and ACE-2 with the right ribbon. FIG. 2B is a simulated structure of SARSCoV2 glycoprotein (left ribbon) that shows similar structure with $L_{6 \to 7}$ loop (enclosed dotted square) interacting with the ACE-2 interface.

Further investigation of H-bonding interactions revealed that, threonine 487 (T487) of SARS-CoV1 and threonine 500 (T500) of SARS-CoV2 engaged multiple H-bond interactions with ACE-2. Furthermore, recently resolved x-ray crystal structure of SARS-COV2 complexed with ACE2 further validated that $L_{6 \to 7}$ peptide sequence surrounding T500 might be crucial for making interactions with ACE-2. Applicants propose that Thr-500 is essential for the binding of the s-glycoprotein and the ACE-2 enzyme. Based on this structural evidence, Applicants propose a peptide FQPTNGVGYQPYG (SEQ ID NO: 1) (herein after referred to as "ACIS" peptide) that can block the interaction of S-glycoprotein and ACE-2 and therefore nullify the biological action of SARS-CoV2.

ACIS Peptide Blocks the Action of SARS-CoV2

Embodiments include a peptide vaccine that can prevent the infection of SARS-CoV2. The peptide (i.e., ACIS) includes 13 amino acids (FQPTNGVGYQPYG) (SEQ ID NO: 1).

The ACIS peptide was designed from a conserved $L_{6 \to 7}$ loop region of S-glycoprotein which connects two adjacent β-strands together. That 13 aa-long loop is critical for the interaction of SARS-CoV2 and ACE-2. Structurally, the $L_{6 \to 7}$ loop is conserved across all different strains of coronaviruses. Therefore, ACIS peptide has a prospect to inhibit infections elicited by other strains of coronaviruses.

FIG. 2C depicts ACIS peptide (center) which inhibits the interaction between SARS-CoV2 S-glycoprotein (left) and ACE-2 (right). The arrows indicate the displacement of S-glycoprotein which is far from the ACE-2 enzyme. Table 2 presents a summary of the hydrogen bonding interactions.

TABLE 2

H-Bond Interactions with ACIS Peptide

| Donor | Acceptor | Distance (Å) |
| --- | --- | --- |
| GLN 42.A NE2 | TYR 505.0 O | 3.573 |
| SER 375.6 OG | GLN 498.0 OE1 | 3.043 |
| PHE 497.0 N | ASN 439.6 OD1 | 2.871 |
| GLN 498.0 NE2 | SER 375.6 OG | 2.917 |
| THR 500.0 OG1 | GLU 57.A O | 2.469 |
| THR 500.0 OG1 | ASN 61.A OD1 | 1.790 |
| TYR 505.0 OH | GLU 38.A OE1 | 2.346 |

A = ACE-2; B = S-Glycoprotein; C = ACIS peptide

The ACIS peptide is specifically designed from the part of S-glycoprotein that is conserved only in the coronaviral family. Because of this specificity there is no possibility of any off-target effect. Moreover, BLAST analysis further confirmed that the peptide does not share any homology with other endogenous protein nullifying the possibility of non-specific action of the peptide. Blitz assay was used to confirm the specificity of ACIS peptide towards ACE-2 protein. BLItz assay between biotin tagged ACIS and full-length ACE-2 revealed that there was a strong affinity of that peptide towards ACE-2 protein with $K_D$=115 nM. The binding was strong as a dose-dependent study demonstrated binding at concentrations as low as 13 nM and rapid as early as 50 seconds of the reaction.

Figure 3A:
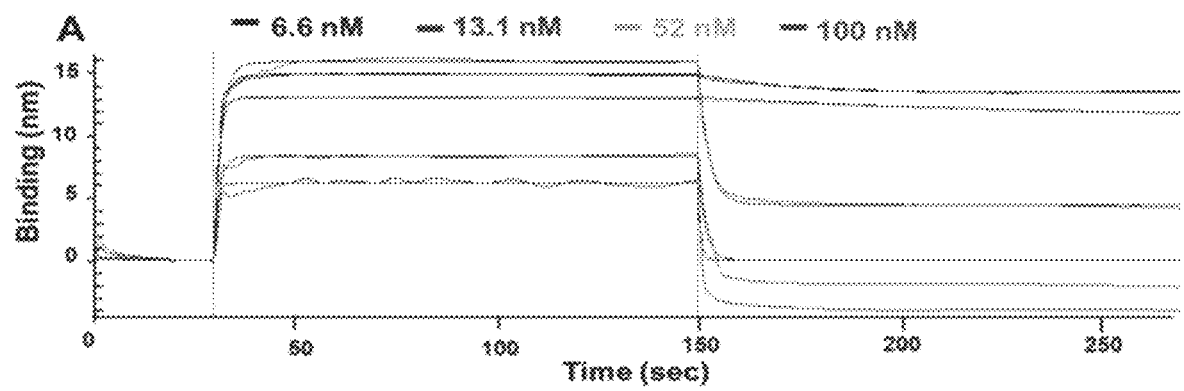
FIG. 3A shows results of a BLItz assay for exploring the affinity of ACIS peptide towards the ACE-2 enzyme.
Figure 3B:
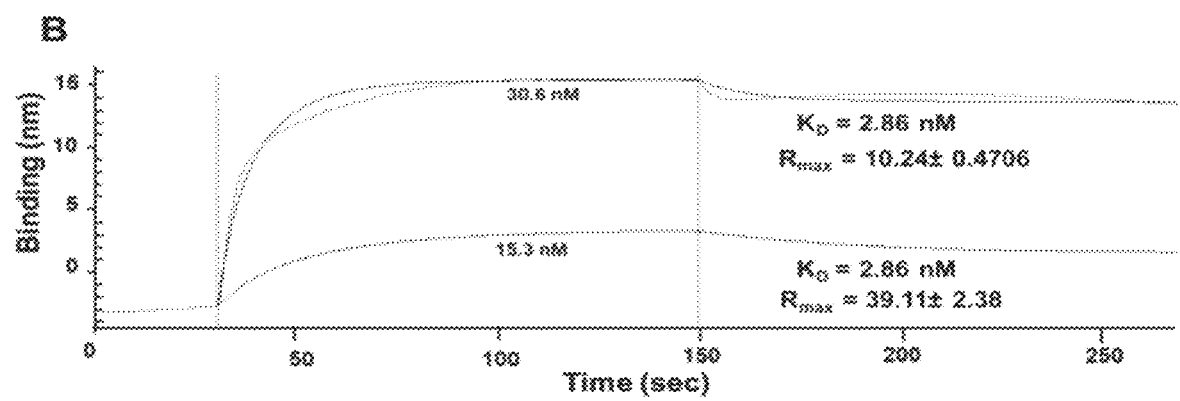
FIG. 3B shows results of a BLItz assay that demonstrates optimum binding was observed at 2.86 nM concentration.
Figure 3C:
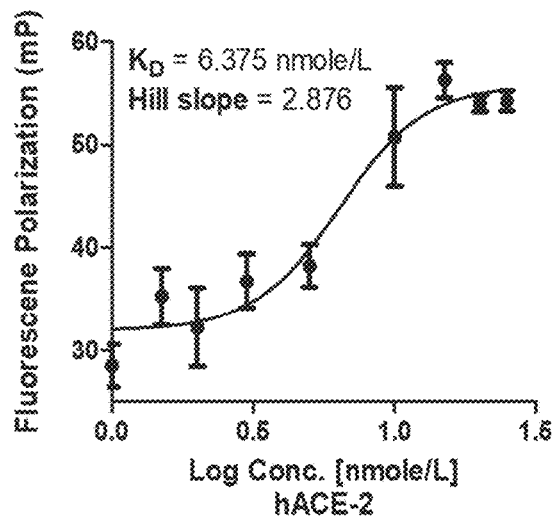
FIG. 3C shows results of experiments of ACIS peptide tagged with FITC probe at C-terminal end, which during testing was designated as KEPTIDE2.

FIG. 3A shows the results of the BLItz assay. BLItz sensor was loaded with ACIS peptide (0.25 µg/µL) followed by titration with different concentrations of ACE-2 enzyme starting from nM range. FIG. 3B shows results of a BLItz assay that demonstrates maximum binding was observed at 2.86 nM concentration. FIG. 3C shows results of fluorescence polarization ("FP") assay that demonstrates that FITC-tagged ACIS peptide binds with ACE-2 at a concentration of 6.376 nM.

Another consideration is the activity of ACE-2. The biological action of ACE-2 enzyme has been well studied. ACE-2 degrades angiotensin-II, a hormone that causes vasoconstriction. Therefore, activation of ACE-2 might stimulate dilation of blood vessels and lower blood pressure. Endogenous peptide hormone angiotensin II, growth factor collectrin and small sugar moiety N-glucosamine bind to the ectodomain of ACE-2. These interactions are not only required for the cellular metabolism of peptide hormones, but also required to retain the catalytic action of ACE-2 in the plasma membrane. Interestingly, that same ectodomain plays a critical role in the interaction with S-glycoprotein of SARS-CoV2. Hence, if a peptide is designed from the ectodomain of ACE-2, then that peptide binds to these biological regulators of ACE-2. Eventually, the catalytic action of ACE-2 will be disrupted. On the other hand, ACIS peptide is designed not from the enzyme, but against a viral protein. Therefore, the peptide is only expected to inhibit the binding of exogenous SARS-CoV2 with ACE-2 enzyme and not to impair the interaction of other endogenous regulators with ACE-2.

Moreover, it is known that ACE-2 is a peptidase. Specifically, ACE-2 is a carboxypeptidase that cleaves carboxy-terminal peptide bond between proline and phenylalanine of angiotensin II. This presents the question of whether it can it cleave the ACIS peptide. The ACIS peptide does not provide that substrate specificity to ACE-2 mitigating the possibility of degradation of ACIS by ACE-2 enzyme.

ACIS Peptide Inhibits the Complex Formation Between ACE-2 and S-Glycoprotein

The inhibitory effect of ACIS peptide on the interaction of S-glycoprotein with ACE-2 receptor was evaluated. The study included chemical modified variants of the ACIS peptide. A C-terminal tag of lysine residue was used to increase the basic property to the peptide. The addition of lysine was also used for chemical modification of peptide with biotin (Vitamin H or B7) and a thienoimidazole derivative (i.e. FITC). The addition of a biotin molecule neutralizes the negative charge of carboxy terminal group and adds positive charge to the peptide. During testing, the biotin-modified KEPTIDE COVID was designated as "KEPTIDE1." Further, "KEPTIDE2" was designated for a FITC tagged KEPTIDE modified with acidic xanthene based compound at the acidic end of the peptide.

Figure 4A:
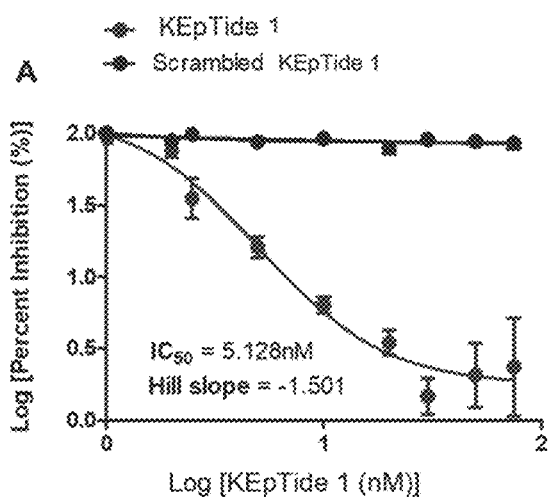
FIGS. 4A and 4B show Effect of ACIS variants KEPTIDE1 and KEPTIDE2 on inhibiting the complex formation between ACE-2 and S-Glycoprotein.
Figure 4B:
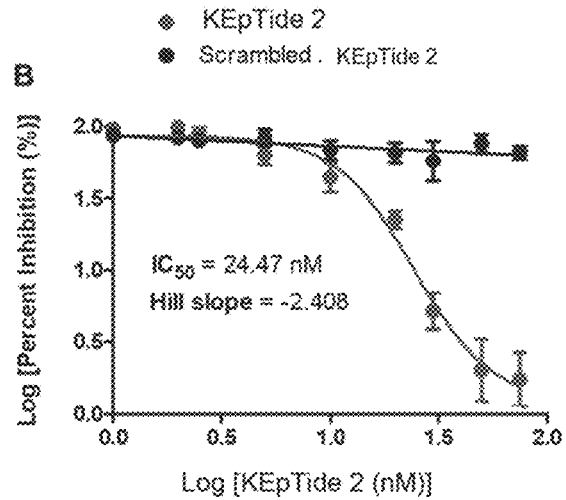

A kit-based luminometric inhibitor screen assay was used to evaluate the efficacy of the biotinylated and FITC labeled ACIS in inhibiting the interaction between S-glycoprotein and ACE-2 protein. Increasing doses of biotinylated- and FITC-labeled ACIS significantly inhibited the association of S-glycoprotein with ACE-2 as indicated with the $IC_{50}$ values of 5.12 nM (FIG. 4A) and 24.47 nM (FIG. 4B) respectively. Moreover, the hillslope of the inhibition plot was significantly steeper in case of biotinylated ACIS (−1.5) compared to FITC-ACIS (−2.4) suggesting that biotinylated-ACIS displayed stronger inhibition than FITC-ACIS. In contrast to sigmoidal binding curve, there was no binding observed in case of scrambled KEPTIDE COVIDs. Taken together, this result suggests that biotinylated-ACIS peptide significantly inhibits the interaction of S-glycoprotein with host ACE-2 protein and that inhibition is observed to be almost five times stronger than FITC-ACIS peptide.

To delineate the effect of KEPTIDE COVID on nullifying the infectivity of the virus, a series of cell culture study in mammalian VERO E6 cells were performed using kidney cells of primate origin that strongly express ACE-2 receptor. Wuhan standard stock of SARS-CoV2 (SARS CoV-2 USA_WA1/2020) was maintained in a FDA-approved laboratory, enriched, titrated and applied on VERO ($5*10^6$ cells per well with 90% confluency) cells at a dose of 1-2 PFU for the infection as described in the materials and methods section below. In ACIS-treatment condition, VERO cells were pre-incubated with 25 μM of ACIS under serum-free condition for 30 minutes followed by the treatment with SARS-CoV2 strain for 2 and 6 hrs. In DMSO control group, VERO cells were treated with equivalent volume of DMSO. Two-hours timepoint was selected to evaluate the efficacy of the peptide to stop acute infection, whereas 6 hours timepoint was selected for nullifying the secondary or chronic infection. After 2 hours of viral incubation, supernatants with infectious virions were harvested from the top of the VERO cells and analyzed from agar monolayer invasion assay as described in method section. Different dilutions (1:20 to 1:800,000) of viral supernatants were applied on agar-coated 96-well plate, neutralized with 10% neutral buffer formalin, and then stained with 2% Crystal Violet (CV) solution in 20% methanol. Viral supernatants of 25 μM ACIS-treated VERO cells, but not DMSO-treated cells, displayed significant damage in agar monolayer as demonstrated in the loss of CV staining at 1:20 and 1:80 dilution series. (FIG. 5A) Supernatants from both KEPTIDE COVID-treated VERO cells generated equivalent damage to the agar monolayer. Further densitometric quantification of CV staining demonstrated that there were almost five-fold loss of agar monolayer in KEPTIDE COVID-treated groups compared to DMSO-treated VERO cells. Plaque assay were performed, wherein ten and twenty-fold dilutions of a virus stock were prepared, and 0.1 ml aliquots were inoculated onto VERO cell monolayers. After 48 hours of infection, VERO cells were covered with agar layer followed by staining with 2% CV. Each infectious particle generated a circular white zone indicative of infected cells whereas uninfected cells displayed strong blue color. (FIG. 5B) From the densitometric quantification analyses, KEPTIDE1 and KEPTIDE2 displayed significantly stronger protection. KEPTIDE1 displayed almost fifteen-fold increase in protection compared to control at 1:20 dilution dose. (FIGS. 5B and 5C) KEPTIDE2 demonstrated a three-fold increase in protection. These results demonstrate that ACIS-treatment significantly attenuated the entry of SARS-CoV2 viral particles in the VERO cells causing their accumulation in the supernatants.

Further confirming the profound activity of KEPTIDE COVIDs in the attenuation of viral infection, a dual immunostaining analyses with ACIS peptide (green) and S-glycoprotein (red) was performed. DAPI staining was carried out to identify big nuclei of VERO cells. After two hours of SARS-CoV2 treatment (1-2 PFU), 25 μM of ACIS peptide was observed to substantially inhibit the entry of viral particles (FIG. 6A), whereas no inhibition was observed in no DMSO, DMSO alone, and scrambled-ACIS-treated control group. The result was further corroborated with a quantification study that clearly indicated a strong inhibition of viral load around ACIS-treated VERO cells (***$p<0.0001$) (FIG. 6B).

In order to evaluate the efficacy of the KEPTIDE COVID in suppressing the secondary or chronic infection of SARS-COV2, testing was performed by dual immunostaining procedure after six hours of viral infection. 25 μM of ACIS continued to repel viral particles significantly from VERO cells (FIG. 7A) even at 6 hours of infection. The effect was further confirmed with a quantitative analysis (FIG. 7B). Moreover, the distribution of KEPTIDE COVID molecule was carefully analyzed after two and six hours of viral incubation, wherein it was observed that ACIS was perfectly aligned on the membrane of VERO cells at two hours, but significant numbers of KEPTIDE COVID molecules were found to be internalized at six hours, thus suggesting that upon binding ACIS might also stimulate the internalization of ACE-2. As a result, the ACIS peptide efficiently inhibits the entry of SARS-CoV2 in host cells.

Experiments were conducted in mice to assess the bioavailability of KEPTIDE COVID in lungs and blood after administration of KEPTIDE COVID. 0.1 mg/Kg bodyweight dose of KEPTIDE COVID was administered intranasally for 0, 0.5, 1, 2, 6, 12 and 24 hours of time (n=6). After each time point, blood and lung tissue of the test subjects were collected and weighed. For complete disintegration and biotin separation, lung tissue was homogenized with trypsin-containing PBS (1:1) for 10 mins at 37° C. The colorimetric HABA-replacement biotin assay (FIGS. 8A and 8B) revealed that the intranasal administration of KEPTIDE COVID increased biotin with increasing time starting from 30 mins to 6 hours timepoint with maximum at 1 hr. The level of biotin was stable after 6 hours of treatment, an indicator that the affinity of KEPTIDE COVID was strong for lung tissue (FIG. 8A). Free biotin was not observed in the blood (FIG. 8B), which suggests that the half-life of biotin in blood is short and/or significant amount of biotin is being washed out through blood in early timepoint before 30 mins.

Figure 9A:
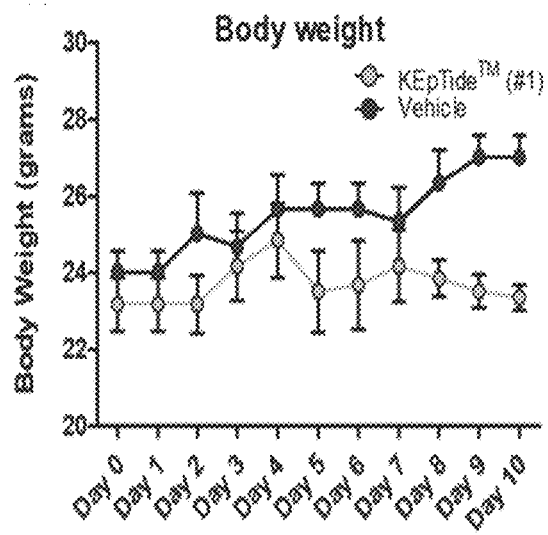
Figure 9C:
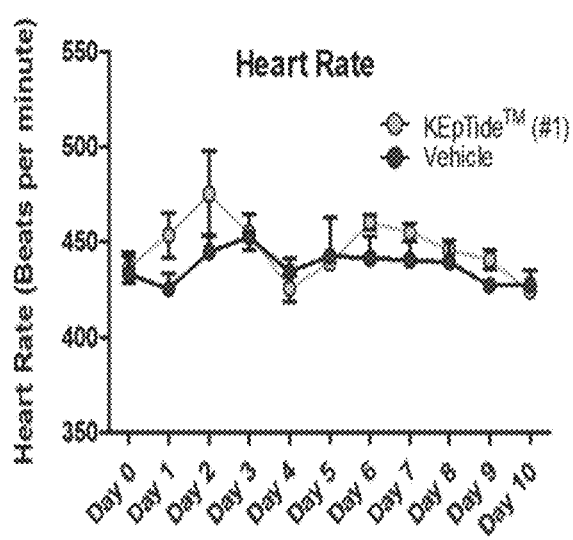
Figure 9B:
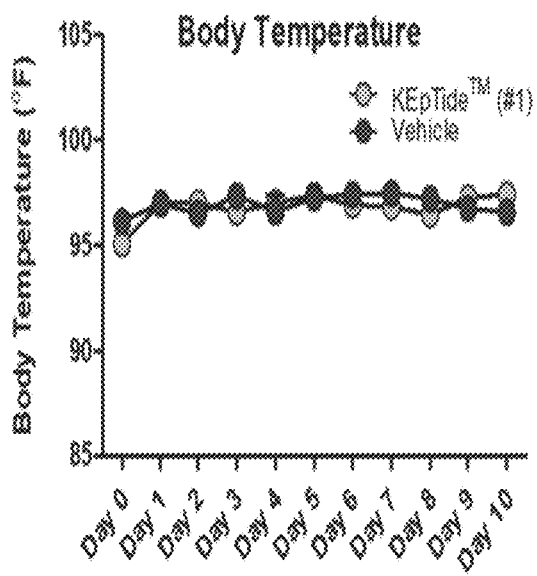
Figure 9D:
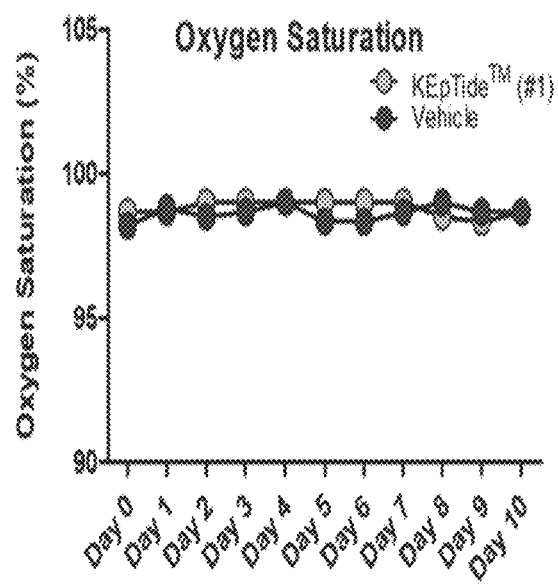

To test whether adversary off-target effects (aka toxicity) are caused by chronic administration of ACIS, tests were conducted to monitor the effects of KEPTIDE COVID in vivo in mice over 10 days period following daily intranasal administration. 0.1 mg/Kg body weight KEPTIDE COVID was administered intranasally to 8-10 weeks old BALB/C mice every day for 10 days. Each day, body weight, body temperature, heart rate, and oxygen saturation were monitored. Other parameters such as skin turgor, diarrhea and respiratory rate were monitored at Day 10. There was no sign of loss in body weight (FIG. 9A), temperature (FIG. 9B), heart rate (FIG. 9C) and respiratory health (FIG. 9D) in these aged BALB/C animals, demonstrating that KEPTIDE COVID does not cause any toxic effects in vivo. Moreover, there were no indications of other health issues such as skin roughness or diarrhea in KEPTIDE COVID-treated BALB/C mice at the end of Day 10. Although change in body weight showed significance (p<0.0008), the result was confounded with two factors. First, the baseline value was low in KEPTIDE-treated animals. Across the treatment regime, KEPTIDE COVID-treated animals did not gain any weight as evident from the comparison of baseline average weight (Day 0) and the weight at the endpoint (Day 10). The average weight remained same throughout KEPTIDE COVID treatment. Second, the saline-treated mice gained significant weight. Therefore, taken together, these results suggest that Biotinylated-ACIS peptide, or KEPTIDE COVID, does not have any toxic off-target effects on health in terms of loss of body weight, hypothermia, hypertension rate and respiratory stress Methods of Use The ACIS peptide and variants can be administered as a nasal spray or inhalant to combat respiratory viruses such as coronaviruses. However, any suitable route or mode of administration can be employed for providing the patient with a therapeutically or prophylactically effective dose of the therapeutic peptide. Exemplary routes or modes of administration include parenteral (e.g., intravenous, intraarterial, intramuscular, subcutaneous, intratumoral), oral, topical (nasal, transdermal, intradermal or intraocular), mucosal {e.g., nasal, sublingual, buccal, rectal, vaginal), inhalation, intralymphatic, intraspinal, intracranial, intraperitoneal, intratracheal, intravesical, intrathecal, enteral, intrapulmonary, intralymphatic, intracavital, intraorbital, intracapsular and transurethral, as well as local delivery by catheter or stent.

A pharmaceutical composition comprising a therapeutic peptide in accordance with the present disclosure can be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions can include suitable solid or gel phase carriers or excipients. Exemplary carriers or excipients include calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases it will be preferable to include isotonic agents, for example, sugars, polyalcohols such as mannitol, sorbitol, or sodium chloride in the composition. Pharmaceutically acceptable carriers can further comprise minor amounts of auxiliary substances such as wetting or emulsifying agents, preservatives or buffers, which enhance the shelf life or effectiveness of the therapeutic agents.

The therapeutic peptide can be incorporated into a pharmaceutical composition suitable for parenteral administration. Suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05%> polysorbate-80 (optimally 0.005-0.01%). Additional surfactants include but are not limited to polysorbate 20 and BRIJ surfactants.

Therapeutic peptide preparations can be lyophilized and stored as sterile powders, preferably under vacuum, and then reconstituted in bacteriostatic water (containing, for example, benzyl alcohol preservative) or in sterile water prior to injection. Pharmaceutical compositions can be formulated for parenteral administration by injection e.g., by bolus injection or continuous infusion.

Preferably, the polypeptide domains in the therapeutic peptide are derived from the same host in which they are to be administered in order to reduce inflammatory responses against the administered therapeutic agents.

The therapeutic peptide can be administered as a preventive measure (i.e. to avoid infection) at one time or multiple times based on, for example, the half-life of the peptide and the likelihood of one's exposure to a coronavirus. Alternatively, the therapeutic peptide is suitably administered to the patient at one time or over a series of treatments and may be administered to the patient at any time from diagnosis onwards. The therapeutic peptide may be administered as the sole treatment or in conjunction with other drugs or therapies useful in treating the condition in question.

Certain embodiments of the invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Administration

A pharmaceutical composition comprising ACIS in accordance with the present disclosure can be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions can include suitable solid or gel phase carriers or excipients. Exemplary carriers or excipients include calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases it will be preferable to include isotonic agents, for example, sugars, polyalcohols such as mannitol, sorbitol, or sodium chloride in the composition. Pharmaceutically acceptable carriers can further comprise minor amounts of auxiliary substances such as wetting or emulsifying agents, preservatives or buffers, which enhance the shelf-life or effectiveness of the therapeutic agents.

The therapeutic agents in the pharmaceutical compositions can be formulated in a "therapeutically effective amount" or a "prophylactically effective amount". A "therapeutically effective amount" refers to an amount effective, at dosages and for periods of time necessary, to achieve the desired therapeutic result. A therapeutically effective amount may vary depending on the condition to be treated, the severity and course of the condition, the mode of administration, whether the agent is administered for preventive or therapeutic purposes, the bioavailability of the particular agent(s), the ability of the therapeutic peptide to elicit a desired response in the individual, previous therapy, the age, weight and sex of the patient, the patient's clinical history and response to the agent, the type of the therapeutic peptide used, discretion of the attending physician, etc. A therapeutically effective amount is also one in which any toxic or detrimental effects is outweighed by the therapeutically beneficial effects. A "prophylactically effective amount" refers to an amount effective, at dosages and for periods of time necessary, to achieve the desired prophylactic result.

The solution containing ACIS is suitably administered to the patient at one time or over a series of treatments and may be administered to the patient at any time from diagnosis onwards. Alternatively, it can be administered as a preventive measure (i.e. to avoid infection). The solution can be administered as the sole treatment or in conjunction with other drugs or therapies useful in treating the condition in question.

As a general proposition, a therapeutically effective amount or prophylactically effective amount of ACIS peptide will be administered in a range from about 1 ng/kg body weight to about 100 mg/kg body weight whether by one or more administrations. In a particular embodiment, each therapeutic peptide is administered in the range of from about 1 ng/kg body weight to about 10 mg/kg body weight, about 1 ng/kg body weight to about 1 mg/kg body weight, about 1 ng/kg body weight to about 100 g/kg body weight, about 1 ng/kg body weight to about 10 g/kg body weight, about 1 ng/kg body weight/day to about 1 g/kg body weight, about 1 ng/kg body weight to about 100 ng/kg body weight, about 1 ng/kg body weight to about 10 ng/kg body weight, about 10 ng/kg body weight to about 100 mg/kg body weight, about 10 ng/kg body weight to about 10 mg/kg body weight, about 10 ng/kg body weight to about 1 mg/kg body weight, about 10 ng/kg body weight/to about 100 g/kg body weight, about 10 ng/kg body weight to about 10 mg/kg body weight, about 10 ng/kg body weight to about 1 mg/kg body weight, 10 ng/kg body weight to about 100 ng/kg body weight, about 100 ng/kg body weight to about 100 mg/kg body weight, about 100 ng/kg body weight to about 10 mg/kg body weight, about 100 ng/kg body weight to about 1 mg/kg body weight, about 100 ng/kg body weight to about 100 mg/kg body weight, about 100 ng/kg body weight to about 10 mg/kg body weight, about 100 ng/kg body weight to about 1 mg/kg body weight, about 1 mg/kg body weight to about 100 mg/kg body weight, about 1 mg/kg body weight to about 10 mg/kg body weight/day, about 1 mg/kg body weight to about 1 mg/kg body weight, about 1 mg/kg body weight to about 100 mg/kg body weight, about 1 mg/kg body weight to about 10 mg/kg body weight, about 10 mg/kg body weight to about 100 mg/kg body weight, about 10 mg/kg body weight to about 10 mg/kg body weight, about 10 mg/kg body weight to about 1 mg/kg body weight/day, about 10 mg/kg body weight to about 100 mg/kg body weight, about 100 mg/kg body weight/day to about 100 mg/kg body weight, about 100 mg/kg body weight/day to about 10 mg/kg body weight, about 100 mg/kg body weight/day to about 1 mg/kg body weight, about 1 mg/kg body weight to about 100 mg/kg body weight, about 1 mg/kg body weight to about 10 mg/kg body weight, about 10 mg/kg body weight to about 100 mg/kg body weight/day.

In other embodiments, ACIS peptide is administered in the range of about 10 ng to about 100 ng per individual administration, about 10 ng to about 1 g per individual administration, about 10 ng to about 10 g per individual administration, about 10 ng to about 100 mg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 mg per individual administration, about 100 ng to about 10 mg per individual administration, about 100 ng to about 100 mg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 mg to about 10 mg per individual administration, about 1 mg to about 100 mg per individual administration, about 1 mg to about 1 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1 mg per individual administration, about 10 mg to about 10 mg per individual administration, about 10 mg to about 100 mg per individual administration, about 10 mg to about 1000 mg per injection, about 10 mg to about 10,000 mg per individual administration, about 100 mg to about 1 mg per individual administration, about 100 mg to about 10 mg per individual administration, about 100 mg to about 100 mg per individual administration, about 100 mg to about 1000 mg per injection, about 100 mg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The therapeutic peptide may be administered daily, every 2, 3, 4, 5, 6, 7 or 10 days, or every 1, 2, 3 or 4 weeks.

In other particular embodiments, the amount of the ACIS peptide can be administered at a dose of about 0.0006 mg, 0.001 mg, 0.003 mg, 0.006 mg, 0.01 mg, 0.03 mg, 0.06 mg, 0.1 mg, 0.3 mg, 0.6 mg, 1 mg, 3 mg, 6 mg, 10 mg, 30 mg, 60 mg, 100 mg, 300 mg, 600 mg, 1000 mg, 2000 mg, 5000 mg or 10,000 mg. As expected, the dosage will be dependent on the condition, size, age and condition of the patient.

In other aspects of this embodiment, a pharmaceutical composition compound disclosed herein reduces the incidence of viral infection (e.g. the basie reproduction ratio) by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a pharmaceutical composition disclosed herein reduces the incidence of viral infection from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition disclosed herein is in an amount sufficient to allow customary administration to an individual. In aspects of this embodiment, a pharmaceutical composition disclosed herein can be, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a pharmaceutical composition. In other aspects of this embodiment, a pharmaceutical composition disclosed herein may be, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a pharmaceutical composition. In yet other aspects of this embodiment, a pharmaceutical composition disclosed herein may be in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a pharmaceutical composition disclosed herein may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

A pharmaceutical composition disclosed herein can comprise a solvent, emulsion or other diluent in an amount sufficient to dissolve a pharmaceutical composition disclosed herein. In other aspects of this embodiment, a pharmaceutical composition disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a pharmaceutical composition disclosed herein may comprise a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

The final concentration of a pharmaceutical composition disclosed herein in a pharmaceutical composition disclosed herein can be of any concentration desired. In an aspect of this embodiment, the final concentration of a pharmaceutical composition in a pharmaceutical composition may be a therapeutically effective amount. In other aspects of this embodiment, the final concentration of a pharmaceutical composition in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL or at least 500 mg/mL. In other aspects of this embodiment, the final concentration of a pharmaceutical composition in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

Aspects of the present specification disclose, in part, treating an individual who is susceptible to viral infection or suffering from viral infection. As used herein, the term "treating," refers to reducing or eliminating the incidence of viral infection; or lowering or depleting the viral load. For example, the term "treating" can mean reducing a symptom of a condition characterized by a viral infection, including, but not limited to, decreasing viral load, by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. Those of skill in the art will know the appropriate symptoms or indicators associated with a specific type of ailment and will know how to determine if an individual is a candidate for treatment as disclosed herein.

In aspects of this embodiment, a therapeutically effective amount of a pharmaceutical composition disclosed herein reduces viral load, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a pharmaceutical composition disclosed herein reduces viral load by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a pharmaceutical composition disclosed herein reduces viral load by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of a pharmaceutical composition disclosed herein generally is in the range of about 0.001 mg/kg to about 100 mg/kg and administered, for example, every 3, 5, 7, 10 or 14 days. In aspects of this embodiment, an effective amount of a pharmaceutical composition disclosed herein may be, e.g., at least 0.001 mg/kg, at least 0.01 mg/kg, at least 0.1 mg/kg, at least 1.0 mg/kg, at least 5.0 mg/kg, at least 10 mg/kg, at least 15 mg/kg, at least 20 mg/kg, at least 25 mg/kg, at least 30 mg/kg, at least 35 mg/kg, at least 40 mg/kg, at least 45 mg/kg, or at least 50 mg/kg and administered, for example, every 3, 5, 7, 10 or 14 days. In other aspects of this embodiment, an effective amount of a pharmaceutical composition disclosed herein may be in the range of, e.g., about 0.001 mg/kg to about 10 mg/kg, about 0.001 mg/kg/day to about 15 mg/kg, about 0.001 mg/kg to about 20 mg/kg, about 0.001 mg/kg to about 25 mg/kg, about 0.001 mg/kg to about 30 mg/kg, about 0.001 mg/kg to about 35 mg/kg, about 0.001 mg/kg to about 40 mg/kg, about 0.001 mg/kg to about 45 mg/kg, about 0.001 mg/kg to about 50 mg/kg, about 0.001 mg/kg to about 75 mg/kg, or about 0.001 mg/kg to about 100 mg/kg and administered, for example, every 3, 5, 7, 10 or 14 days. In yet other aspects of this embodiment, an effective amount of a pharmaceutical composition disclosed herein may be in the range of, e.g., about 0.01 mg/kg to about 10 mg/kg, about 0.01 mg/kg to about 15 mg/kg, about 0.01 mg/kg to about 20 mg/kg, about 0.01 mg/kg to about 25 mg/kg, about 0.01 mg/kg to about 30 mg/kg, about 0.01 mg/kg to about 35 mg/kg, about 0.01 mg/kg to about 40 mg/kg, about 0.01 mg/kg to about 45 mg/kg, about 0.01 mg/kg to about 50 mg/kg, about 0.01 mg/kg to about 75 mg/kg, or about 0.01 mg/kg to about 100 mg/kg and administered, for example, every 3, 5, 7, 10 or 14 days. In still other aspects of this embodiment, an effective amount of a pharmaceutical composition disclosed herein may be in the range of, e.g., about 0.1 mg/kg to about 10 mg/kg, about 0.1 mg/kg to about 15 mg/kg, about 0.1 mg/kg to about 20 mg/kg, about 0.1 mg/kg to about 25 mg/kg, about 0.1 mg/kg to about 30 mg/kg, about 0.1 mg/kg to about 35 mg/kg, about 0.1 mg/kg to about 40 mg/kg, about 0.1 mg/kg to about 45 mg/kg, about 0.1 mg/kg to about 50 mg/kg, about 0.1 mg/kg to about 75 mg/kg, or about 0.1 mg/kg to about 100 mg/kg and administered, for example, every 3, 5, 7, 10 or 14 days.

Dosing can be single dosage or cumulative (serial dosing), and can be readily determined by one skilled in the art. For example, treatment of a viral infection can comprise a one-time administration of an effective dose of a pharmaceutical composition disclosed herein. Alternatively, treatment of viral infection may include multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms and/or viral load. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

In one embodiment, a therapeutic disclosed herein is capable of reducing the incidence of viral infection by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, viral load in an individual is decreased by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In a further embodiment, the therapeutic peptide and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, the period of administration of a viral therapeutic is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In aspects of this embodiment, a therapeutically effective amount of a therapeutic disclosed herein reduces the incidence of viral infection by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic disclosed herein reduces the incidence of viral infection by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic disclosed herein reduces the incidence of viral infection by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In an embodiment, treatment with ACIS peptide decreases the average basic reproduction number or $R_0$ by at least 0.5, least 1, at least 2, at least 3, about 0.5, about 1, about 2 or about 3.

EXAMPLES

The following non-limiting examples are provided for illustrative purposes only in order to facilitate a more complete understanding of representative embodiments now contemplated. These examples are intended to be a mere subset of all possible contexts in which the components of the formulation may be combined. Thus, these examples should not be construed to limit any of the embodiments described in the present specification, including those pertaining to the type and amounts of components of the formulation and/or methods and uses thereof Applicants performed a series of assays including fluorescence polarization, surface plasmon resonance and a bio-layer inferometric BLItz assay to understand the kinetics of interaction between ACE-2 and ACIS. The affinity of interaction was then validated with different kinetic constants such as KD, ka and Rmax. Based on these results, Applicants confirmed that ACIS was a high-affinity peptide inhibitor that can block the infection of SARS-CoV2. It is a promising therapy to use against the global pandemic of COVID-19.

Example 1

Determining 3D Structure of S-Glycoprotein of COVID-19

To understand the structural details of S-glycoprotein, Applicants adopted in silico homology modeling strategy to build three-dimensional (3D) structure of S-glycoprotein. An initial structure was modeled by Swiss-Model server, which is operated with a program known as Deep View 3.7β2, an online macromolecular analytical tool of Expert Protein Analytical System (ExPASy). The sequence of S-glycoprotein was derived in FASTA format from the sequence available in PubMed with accession number QIC53213.1 and GI number 1811294675. Swiss-Model generated 3D structure based on the homology of spike protein of coronavirus-1 (PDB ID: 3SCL). The quality of the modeled structure had been evaluated with Quality Measurement Analysis tool (QMEAN) score −2.25. QMEAN is a composite scoring tool that estimates the global quality of the entire model as well as the local per-residue analysis of different regions within a model. Residue-level interaction was evaluated by Cβ atom potential and long-range interactions were validated by all-atom potential. A solvation potential was implemented to analyze the burial status of the residues. The local geometry of the derived structure was analyzed by a torsion angle potential over three consecutive amino acids. Based on all these energy scores, the best predicted structures of S-glycoprotein was achieved.

Molecular Docking of ACE-2 Protein with ACIS Peptide

Molecular docking of ACE-2 protein with ACIS peptide: In order to understand the interaction between ACIS peptide and ACE-2 in a molecular level, Pydock, a rigid body protein-protein docking tool had been applied. The most stable docked structure had been resolved based on electrostatic ($E_{ele}$), desolvation ($E_{desolv}$) and Van der Waals ($\Delta G_{VDW}$) energies and finally displayed with Chimera software. According to that analysis, ACIS peptide was found to be docked in the interface of Spike glycoprotein and ACE-2 protein.

BLItz Assay

Binding kinetics of ACIS with ACE-2 were analyzed using a BLItz™ system (ForteBio, USA) and displayed using the BLItz Pro™ software. The experiment was performed based on manufacturer's instructions. Briefly, biotinylated ACIS peptide was bound to the BLItz streptavidin-linked biosensor. Different doses of ACE-2 enzyme were then charged to the ACIS peptide and then washed.

Example 2

SARS-CoV1 and SARS-CoV2 Share Similar Assembly with ACE-2

Recent studies indicate that SARS-CoV2 engages receptor enzyme ACE2 of host to infect target cells. In fact, a Cryo-EM study clearly identified that spike (S)-glycoprotein complex of SARS-CoV1 (Coronavirus-1) directly interacted with ACE-2. Therefore, neutralizing that interaction might have therapeutic prospect to prevent COVID-19 infection. Three-dimensional structure of ACE-2 and S-glycoprotein of SARS-CoV1 was recently resolved (PDB ID: 3SCL). According to the crystal structure, the loop ($L_{6\rightarrow 7}$) between 6th and 7th β-strands of S-glycoprotein strongly interacts with ACE-2 in its conserved α-helix adjacent to a β-sheet motif (FIG. 1A). Multiple hydrogen bonds (H-bonds) were formed between two proteins at less than 3 Å distance as demonstrated in chimera software. These bonds were summarized and are presented in the table I above.

Thr486 of S-glycoprotein was the key residue that makes H-bond with ACE-2. Accordingly, the strongest H-bond was observed between Thr486 of S-glycoprotein (FIG. 1A) and Tyr41 of ACE-2 at a distance of 2.433 Å. Tyr484, an adjacent residue of Thr486, was also found to engage with Gln42 of ACE-2, however, via a moderately strong H-bond interaction (3.042 Å). Considering all different non-ionic interactions together, Thr486 of S-glycoprotein was observed to be critical for forming H-bond interactions of SARS-CoV1 with ACE-2.

However, COVID-19 pandemic is caused by anther strain of coronavirus, SARS-CoV2 or coronavirus 2. Although both coronavirus-1 and coronavirus 2 share almost 93% sequence homology in S-glycoprotein, it was not clear if SARS-CoV2 displayed similar complex formation with ACE2 because there was significant sequence disparity in $L_{6\to7}$ loops of two viruses. To address this concern, Applicants adopted a homology modeling analysis followed by a PyDock-based rigid-body docking strategy to resolve the complex formation of SARS-CoV2 and ACE-2 protein. To enhance the confidence of the prediction, structural restraints were incorporated in the same stretches of amino acids located in $L_{6\to7}$ loop. Interestingly, a similar structural outcome was derived for SARS-CoV2 S-glycoprotein while forming complex with ACE-2 enzyme (FIG. 2B). Specifically, a tridecapeptide in $L_{6\to7}$ loop of SARS-CoV2 with the sequence of $^{497}$FQPTNGVGYQPYG$^{509}$ intimately engaged in interactions with ACE-2 protein. Similar to Thr486 of SARS-CoV (FIG. 2A), Thr500 of SARS-CoV2 (FIG. 2B) is critical to form complex between S-glycoprotein and ACE-2.

Example 3

Designing ACIS Peptide

After determining the structural hallmark of the interaction between ACE-2 and S-glycoprotein, the next goal was to design a blocking peptide. Applicants proposed a tridecapeptide with the sequence of $^{497}$FQPTNGVGYQPYG$^{509}$ (SEQ ID NO: 1). The peptide is named as ACE-2 Interacting motif of S-glycoprotein or "ACIS" peptide. To nullify the possibility of off-target effects, the homology of the peptide was searched against other host proteins with protein BLAST tool at NCBI server. Interestingly, the BLAST result followed by constraint-based multiple alignment analysis displayed no homology with any other protein except S-glycoprotein indicating that ACIS peptide might exhibit a target-specific action of neutralizing the interaction between Coronavirus2 and ACE-2 enzyme. To further confirm this, a PyDock rigid-body structural analysis was used to verify if ACIS peptide could block the interaction between ACE-2 and S-glycoprotein. Strikingly, the peptide was found to have significantly impaired the interaction between ACE-2 and S-glycoprotein (FIG. 2C). In the presence of that peptide the entire $L_{6\to7}$ loop was shifted far from the conserved β-sheet motif of ACE-2 enzyme. The peptide formed multiple strong H-bond interactions (Table 2) with ACE-2 enzyme nullifying the possibility to be outcompeted by S-glycoprotein. In fact, the ACIS peptide was shown to engage its Thr500 residue for multiple strong H-bonds (bond length less than 2.5 Å) with ACE-2 causing the repulsion of S-Glycoprotein from its original binding pose with ACE-2. Taken together, the results indicate that ACIS peptide is likely to have therapeutic benefits against SARS-CoV2.

In a further embodiment, certain portions of the peptide sequence can be modified such that the loop structure is maintained, and the variant is sufficient to block the interaction of surface glycoprotein on SARS-CoV2 with ACE-2 of host cells. One such embodiment includes modifying the amino acids QPYG, as understood by one of ordinary skill in the art, in a way that maintains the appropriate loop structure to block the interaction of the SARS-CoV2 with ACE-2.

Example 4

Exploring Physical Interaction Between ACIS and ACE-2:

To further characterize the binding between ACIS and ACE-2, BLItz label-free bio-layer interferometry assay was performed. ACIS (0.25 μg/μL) was loaded to the sensor and titrated with different concentration of ACE-2 protein starting with the concentration as low as 10 nM. FIG. 3A shows a BLItz assay for exploring the affinity of ACIS peptide towards the ACE-2 enzyme. BLItz sensor was loaded with ACIS peptide (0.25 μg/μL) followed by titration with different concentrations of ACE-2 enzyme starting from nM range. FIG. 3B shows a BLItz assay that demonstrates maximum binding was observed at 680 nM concentration.

Interestingly, increasing doses of ACIS peptide displayed a dose-dependent binding with full-length ACE-2 protein at a minimum concentration of 13 nM (FIG. 3A) reaching saturation at 680 nM suggesting that ACIS displays a very strong affinity with ACE-2 enzyme. The binding affinity was further validated with strong dissociation constant $(K_D)$=115 nM. Taken together, the results suggest that ACIS can be a strong peptide inhibitor that binds to the ACE-2 enzyme. This can prevent or inhibit the infection of a host cell by SARS-CoV2 virus.

Example 5

In Vitro Cell Culture Validation Studies to Characterize ACIS-Mediated Inhibition of SARS-CoV Infection A biophysical study known as surface plasmon resonance (SPR) was conducted to test the binding efficacy of ACIS peptide with ACE-2 enzyme. As a negative control a mutated version of ACIS peptide was included. The results demonstrated that ACIS prevented binding of viral particles to ACE-2.

Surface plasmon resonance experiment (SPR) was conducted to test the binding efficacy of ACIS peptide with ACE-2 enzyme. For analyte association, different concentrations of ACIS were used along with a mutated ACIS peptide (control). ACIS peptide displayed a strong interaction with ACE-2 enzyme as indicated with a hyperbolic binding curve. Increasing doses of peptide exhibited increasing slope value indicating a strong interaction with ACE-2.

Example 6

In Vitro Cell Culture Validation Studies to Determine the Therapeutic Efficiency of ACIS This experiment will be conducted to verify if ACIS peptide inhibits SARS-CoV infection in human lung epithelial cells that strongly express ACE-2 the receptor of SARS CoV. This in vitro study will be performed in two different sub-aims. In sub-aim I, we will test if ACIS peptide could inhibit S-glycoprotein mediated activation of ACE-2 receptor. In sub-aim II, we will verify if ACIS peptide can prevent SARS-CoV from infecting lung epithelial cells.

Normal Lung epithelial cell line (BEAS-2B; Cat #CRL-9609: Vendor ATCC) will be treated with SARS-CoV-2 viral particles with different multiplicity of infections (MOIs). After two hours of treatment, cells should be thoroughly washed, lysed and then genotyped for viral mRNA with standard RT-PCR using sense and anti-sense primers of S-glycoprotein mRNA. Treatment with ACIS peptide should attenuate the detection of viral mRNA in lung epithelial cells suggesting the loss of entry of viral particles in host cells.

Control or mutated peptide will also be tested to see if they are unable to inhibit the entry of viral particles in host cells because of successful amplification of viral mRNA in host cells.

Example 7

Administration of ACIS Peptide to Prevent SARS-CoV-2 Infection

Due to strong hydrophobicity ACIS peptide is readily soluble in aromatic solvent and therefore can be administered with a nasal spray, metered dose inhaler (MDI) or nebulizer. These modes allow the ACIS peptide to be directly delivered to the lungs. Mucoadhesive and viscosity increasing agents (e.g. pectin and chitosan) can be used to increase drug residence time in the nasal cavity, olfactory epithelium and respiratory system.

Because the ACIS peptide was designed from the part of S-glycoprotein, it prevents infection without deleterious or unwanted side effects. Based on the half-life, it can be administered regularly (e.g. daily) to a patient who is susceptible to infection.

Example 8

Administration of KEPTIDE to Prevent SARS-CoV-2 Infection

Chemically modified variants of ACIS peptide can be used in a manner as described above. For example, a C-terminal tag of lysine residue can be added to the peptide to increase its basicity. The addition of biotin (Vitamin H or B7) to the peptide (KEPTIDE1) can improve activity. Similarly the addition of FITC can improve activity also (KEPTIDE2).

As in the above example, the KEPTIDE can be administered with a nasal spray, metered dose inhaler (MDI) or nebulizer. This allows the peptide to be directly delivered to the lungs. Mucoadhesive and viscosity increasing agents (e.g. pectin and chitosan) can be used to increase drug residence time in the nasal cavity, olfactory epithelium and respiratory system.

The KEPTIDE can prevent infection without deleterious or unwanted side effects. Based on the half-life, it can be administered regularly (e.g. daily) to a patient who is susceptible to infection.

One aspect of the invention are peptides identified as SEQ ID NO: 1 and SEQ ID NO: 2.

tion, the media was changed to complete media supplemented with 2% heat inactivated FBS. After 72 hours of infection, viral stock (Media of T75 flask) was harvested and RT-PCR was run to quantify the genomic equivalent. To test the effect of ACIS peptide on the CPE of viral particles, 5× 10% VERO cells were treated with 25 µM of ACIS or equivalent DMSO for 30 mins under serum-free condition. After that, unbound ACIS was aspirated followed by the infection with 1-2 genomic equivalent of SARS-CoV2 for 2 hrs. After 2 hours, supernatants were harvested and applied in an agar monolayer-coated 96-well plates at different dilutions starting from 1:20 to 1:800,000. The supernatants were kept at 37° C. for 72 hours, aspirated and fixed with 10% formalin for 30 mins at room temperature. Once the formalin is aspirated, 2% Crystal Violet solution (v/v n 20% methanol) was added in each well for 5 mins, rinsed and dried. The CPE was monitored by counting the extent and numbers of holes in the agar monolayer.

SARS-CoV2 infectious titer was analyzed by plaque assay with slight modifications. VERO cells were split into 6 well culture plates at the concentration of $5 \times 10^5$ cells/well. An aliquot of SARS-CoV2 stocks was thawed and then 100-fold serially diluted in the culture media starting from 1:20 fold dilution. VERO E6 cells were pre-incubated with DMSO, 25 µM of KEpTide 1 and 2 for 30 mins and then inoculated with 500 µL of each SARS-CoV2 dilution and incubated at 37° C. for 1 hour with rocking every 15 min. The inoculum was removed, and the cells were washed once with 1×PBS to eliminate the unbound virus particles. The cells were overlaid with overlay media containing 1.25 µg/mL acetylated trypsin and 0.8% (w/v) agarose (Lonza) and additionally incubated at 37° C. for 72 hours. Cells were fixed and stained in 20% ethanol containing 2% crystal violet at room temperature for 15 min to visualize the plaques. The infectious particles were counted per well, normalized with the dilution factor, and counted as a number of infected particles per mL of inoculum. The data represent the mean±standard error of four independent experiments.

Double Immunocytochemistry analyses was performed where 5×106 VERO Cells were plated per well in 8-well chamber slide. Cells were starved with serum-free DMEM media for 30 mins followed by the treatment with 25 µM FITC-labeled KEPTIDE COVID. After another 30 mins, unbound KEPTIDE COVIDs were aspirated and then added SARS-CoV2 at a dose of 1-2 PFU/cell. After 2 and 6 hours of virus treatment, viral cells were removed, VERO cells were fixed with 8% PFA and kept at 4° C. for overnight.

TABLE 3

Peptide Sequences

| SEQ ID NO: | Peptide Sequence | Description |
|---|---|---|
| 1 | FQPTNGVGYQPYG | $L_{6 \to 7}$ loop of SARS-CoV2/ACIS Peptide |
| 2 | FYTTTGIGYQP | $L_{6 \to 7}$ loop of SARS-CoV1 |

Materials and Methods

Measurement of Cytopathic Effect (CPE) of SARS-COV2 from the supernatant of ACIS-treated VERO Cells was performed. Viral stock was made by infecting 90% confluent VERO cells with 5×105 PFU SARS-CoV2 Wuhan standard (SARS CoV-2 USA_WA1/2020) at a MOI of 0.025. VERO cells were grown in Growth in complete DMEM media supplemented with 10% FBS. Before infec- Next day, cells were washed with 1×PBS followed by blocking with 2% horse serum, incubation with primary antibody (1:500 dilution with 1×PBS-tween) for 2 hours at 37° C., washed with 1×PBS, incubated with 2° antibody (1:250 dilution at PBST combined with 1% horse serum). Cells were washed with PBS three times with DAPI (1:10000 dilution in water) at final wash. Slide was covered with coverslip and then dried at room temperature at dark.

Next day, the cells were imaged in BX51 Olympus microscope at UIC RRC core facility.

Biotin assay was also performed using eight to ten weeks-old BALB/C mouse administered with KEPTIDE COVID at a dose of 0.1 mg/Kg body weight intranasally. The mice were anesthetized with Ketamine-Xylazine mixture followed by administration of 2 µL of KEPTIDE COVID in each nostril. The KEPTIDE COVID was inoculated for 0 min, 30 mins, 1, 2, 6, 12 and 24 hours (n=3 per group). After that, the mice were evaluated for biotin in blood and lungs. Lung tissue was disintegrated with 1×PBS: Trypsin (1:1) solution for 10 mins in 37° C. followed by homogenization and centrifugation at 12000 rpm for 5 mins. Blood serum was collected in EDTA tube. Twenty µL of serum and tissue lysate was assessed for free biotin as per manufacture's protocol of a colorimetric Biotin assay Kit (AAT Bioquest; Cat #5522). The reduction of absorbance value was recorded once biotin of the sample replaced HABA (4'-hydroxyazobenzene-2-carboxylic acid) from HABA-avidin complex. The assay was performed and recorded in a 96 well plate format of EPOCH Biotek plate reader. The endpoint absorbance wavelength was 500 nm and the final absorbance was recorded in Gen5 software version 2.05.

Intranasal administration of KEPTIDE COVID and monitoring health-related side-effects in BALB/C Mice after intranasal administration of KEPTIDE COVID were observed. Eight to ten weeks-old BALB/C mouse were administered with KEPTIDE COVID at a dose of 0.1 mg/Kg body weight. A single dose of KEPTIDE COVID and saline (control) was administered through intranasal route (2.5 µL each nostril=total 5 µL) each day for 7 days (n=6 per group; 3 male and 3 female). For controlled intranasal delivery of drug, each time micropipette was loaded with 2.5 µL of KEPTIDE COVID and dispensed through nasal cavity by firmly holding mouse in the palm. Every day, mice were monitored for their overall health such as body weight. temperature, heart rate, oxygen saturation, skin tone and diarrhea. The body weight was monitored with digital scale (CAMRY), whereas body temperature, heart rate and oxygen saturation were monitored with WENSUIJIA Vet health monitor.

In one embodiment, the dose of the composition may be administered daily, semi-weekly, weekly, bi-weekly, or monthly. The period of treatment may be for a week, two weeks, a month, two months, four months, six months, eight months, a year, or longer. The initial dose may be larger than a sustaining dose. In one embodiment, the dose ranges from a weekly dose of at least 0.01 mg/kg, at least 0.25 mg/kg, at least 0.3 mg/kg, at least 0.5 mg/kg, at least 0.75 mg/kg, at least 1 mg/kg, at least 2 mg/kg, at least 3 mg/kg, at least 4 mg/kg, at least 5 mg/kg, at least 6 mg/kg, at least 7 mg/kg, at least 8 mg/kg, at least 9 mg/kg, at least 10 mg/kg, at least 15 mg/kg, at least 20 mg/kg, at least 25 mg/kg, or at least 30 mg/kg In one embodiment, a weekly dose may be at most 1.5 mg/kg, at most 2 mg/kg, at most 2.5 mg/kg, at most 3 mg/kg, at most 4 mg/kg, at most 5 mg/kg, at most 6 mg/kg, at most 7 mg/kg, at most 8 mg/kg, at most 9 mg/kg, at most 10 mg/kg, at most 15 mg/kg, at most 20 mg/kg, at most 25 mg/kg, or at most 30 mg/kg. In a particular aspect, the weekly dose may range from 5 mg/kg to 20 mg/kg. In an alternative aspect, the weekly dose may range from 10 mg/kg to 15 mg/kg.

The present specification also provides a pharmaceutical composition for the administration to a subject. The pharmaceutical composition disclosed herein may further include a pharmaceutically acceptable carrier, excipient, or diluent. As used herein, the term "pharmaceutically acceptable" means that the composition is sufficient to achieve the therapeutic effects without deleterious side effects, and may be readily determined depending on the type of the diseases, the patient's age, body weight, health conditions, gender, and drug sensitivity, administration route, administration mode, administration frequency, duration of treatment, drugs used in combination or coincident with the composition disclosed herein, and other factors known in medicine.

The pharmaceutical composition herein may further include a pharmaceutically acceptable carrier. For oral administration, the carrier may include, but is not limited to, a binder, a lubricant, a disintegrant, an excipient, a solubilizer, a dispersing agent, a stabilizer, a suspending agent, a colorant, and a flavorant. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The disclosed compositions may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

On the other hand, examples of the carrier, the excipient, and the diluent suitable for the pharmaceutical formulations include, without limitation, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

Further, the pharmaceutical composition disclosed herein may have any formulation selected from the group consisting of tablets, pills, powders, granules, capsules, suspensions, liquids for internal use, emulsions, syrups, sterile aqueous solutions, non-aqueous solvents, lyophilized formulations and suppositories.

The composition may be formulated into a single dosage form suitable for the patient's body, and preferably is formulated into a preparation useful for peptide drugs according to the typical method in the pharmaceutical field so as to be administered by an oral or parenteral route such as through skin, intravenous, intramuscular, intra-arterial, intramedullary, intramedullary, intraventricular, pulmonary, transdermal, subcutaneous, intraperitoneal, intranasal, intracolonic, topical, sublingual, vaginal, or rectal administration, but is not limited thereto.

The composition may be used by blending with a variety of pharmaceutically acceptable carriers such as physiological saline or organic solvents. In order to increase the stability or absorptivity, carbohydrates such as glucose, sucrose or dextrans, antioxidants such as ascorbic acid or glutathione, chelating agents, low molecular weight proteins or other stabilizers may be used.

The administration dose and frequency of the pharmaceutical composition disclosed herein are determined by the type of active ingredient, together with various factors such as the disease to be treated, administration route, patient's age, gender, and body weight, and disease severity.

The total effective dose of the compositions disclosed herein may be administered to a patient in a single dose, or may be administered for a long period of time in multiple doses according to a fractionated treatment protocol. In the pharmaceutical composition disclosed herein, the content of active ingredient may vary depending on the disease severity. Preferably, the total daily dose of the peptide disclosed herein may be approximately 0.0001 µg to 500 mg per 1 kg of body weight of a patient. However, the effective dose of the peptide is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition disclosed herein. The pharmaceutical composition disclosed herein is not particularly limited to the formulation, and administration route and mode, as long as it shows suitable effects.

Moreover, the pharmaceutical composition may be administered alone or in combination or coincident with other pharmaceutical formulations showing prophylactic or therapeutic efficacy.

Given the teachings and guidance provided herein, those skilled in the art will understand that a formulation described herein can be equally applicable to many types of biopharmaceuticals, including those exemplified, as well as others known in the art. Given the teachings and guidance provided herein, those skilled in the art also will understand that the selection of, for example, type(s) or and/or amount(s) of one or more excipients, surfactants and/or optional components can be made based on the chemical and functional compatibility with the biopharmaceutical to be formulated and/or the mode of administration as well as other chemical, functional, physiological and/or medical factors well known in the art. For example, non-reducing sugars exhibit favorable excipient properties when used with polypeptide biopharmaceuticals compared to reducing sugars. Accordingly, exemplary formulations are exemplified further herein with reference to polypeptide biopharmaceuticals. However, the range of applicability, chemical and physical properties, considerations and methodology applied to polypeptide biopharmaceutical can be similarly applicable to biopharmaceuticals other than polypeptide biopharmaceuticals.

In various embodiments, a formulation can include, without limitation, combinations of bioactive agents (such as viruses, proteins, antibodies, peptides and the like as described herein) in the formulation. For example, a formulation as described herein can include a single bioactive agent for treatment of one or more conditions, including without limitation, disease. A formulation as described herein also can include, in an embodiment, without limitation, two or more different bioactive agents for a single or multiple conditions. Use of multiple bioactive agents in a formulation can be directed to, for example, the same or different indications. Similarly, in another embodiment, multiple bioactive agents can be used in a formulation to treat, for example, both a pathological condition and one or more side effects caused by the primary treatment. In a further embodiment, multiple bioactive agents also can be included, without limitation, in a formulation as described herein to accomplish different medical purposes including, for example, simultaneous treatment and monitoring of the progression of the pathological condition. In an additional embodiment, multiple, concurrent therapies such as those exemplified herein as well as other combinations well known in the art are particularly useful for patient compliance because a single formulation can be sufficient for some or all suggested treatments and/or diagnosis. Those skilled in the art will know those bioactive agents that can be admixed for a wide range of combination therapies. Similarly, in various embodiments, a formulation can be used with a small molecule drug and combinations of one or more bioactive agents together with one or more small molecule pharmaceuticals. Therefore, in various embodiments a formulation is provided containing 1, 2, 3, 4, 5 or 6 or more different bioactive agents, as well as, for one or more bioactive agents combined with one or more small molecule pharmaceuticals.

In various embodiments, a formulation can include, one or more preservatives and/or additives known in the art. Similarly, a formulation can further be formulated, without limitation, into any of various known delivery formulations. For example, in an embodiment, a formulation can include, surfactants, adjuvant, biodegradable polymers, hydrogels, etc., such optional components, their chemical and functional characteristics are known in the art. Similarly known in the art are formulations that facilitate rapid, sustained or delayed release of the bioactive agents after administration. A formulation as described can be produced to include these or other formulation components known in the art.

The composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In various embodiments, the bioactive agents in formulations described herein can, without limitation, be administered to patients throughout an extended time period, such as chronic administration for a chronic condition. The composition can be a solid, a semi-solid or an aerosol and a pharmaceutical compositions is formulated as a tablet, geltab, lozenge, orally dissolved strip, capsule, syrup, oral suspension, emulsion, granule, sprinkle or pellet.

In an embodiment, for oral, rectal, vaginal, parenteral, pulmonary, sublingual and/or intranasal delivery formulations, tablets can be made by compression or molding, optionally with one or more accessory ingredients or additives. In an embodiment, compressed tablets are prepared, for example, by compressing in a suitable tableting machine, the active ingredients in a free-flowing form such as a powder or granules, optionally mixed with a binder (for example, without limitation, povidone, gelatin, hydroxypropylmethyl cellulose), lubricant, inert diluent, preservative, disintegrant (for example, without limitation, sodium starch glycolate, cross-linked povidone, cross-linked sodium carboxymethyl cellulose) and/or surface-active or dispersing agent.

In an embodiment, molded tablets are made, for example, without limitation, by molding in a suitable tableting machine, a mixture of powdered compounds moistened with an inert liquid diluent. In an embodiment, the tablets may optionally be coated or scored, and may be formulated so as to provide slow or controlled release of the active ingredients, using, for example, without limitation, hydroxypropylmethyl cellulose in varying proportions to provide the desired release profile. In an embodiment, tablets may optionally be provided with a coating, without limitation, such as a thin film, sugar coating, or an enteric coating to provide release in parts of the gut other than the stomach. In an embodiment, processes, equipment, and toll manufacturers for tablet and capsule making are well-known in the art.

In an embodiment, capsule formulations can utilize either hard or soft capsules, including, without limitation, gelatin capsules or vegetarian capsules such as those made out of hydroxymethylpropylcellulose (HMPC). In an embodiment, a type of capsule is a gelatin capsule. In an embodiment, capsules may be filled using a capsule filling machine such as, without limitation, those available from commercial suppliers such as Miranda International or employing capsule manufacturing techniques well-known in the industry, as described in detail in Pharmaceutical Capules, 2.sup.nd Ed., F. Podczeck and B. Jones, 2004. In an embodiment, capsule formulations may be prepared, without limitation, using a toll manufacturing center such as the Chao Center for Industrial Pharmacy & Contract Manufacturing, located at Purdue Research Park.

Packaging and instruments for administration may be determined by a variety of considerations, such as, without limitation, the volume of material to be administered, the conditions for storage, whether skilled healthcare practitioners will administer or patient self-compliance, the dosage regime, the geopolitical environment (e.g., exposure to extreme conditions of temperature for developing nations), and other practical considerations.

Injection devices include pen injectors, auto injectors, safety syringes, injection pumps, infusion pumps, glass prefilled syringes, plastic prefilled syringes and needle free injectors syringes may be prefilled with liquid, or may be dual chambered, for example, for use with lyophilized material. An example of a syringe for such use is the Lyo-Ject™, a dual-chamber pre-filled lyosyringe available from Vetter GmbH, Ravensburg, Germany. Another example is the LyoTip which is a prefilled syringe designed to conveniently deliver lyophilized formulations available from LyoTip, Inc., Camarillo, California, U.S.A. Administration by injection may be, without limitation intravenous, intramuscular, intraperitoneal, or subcutaneous, as appropriate. Administrations by non-injection route may be, without limitation, nasal, oral, cocular, dermal, or pulmonary, as appropriate.

In certain embodiments, kits can comprise, without limitation, one or more single or multi-chambered syringes (e.g., liquid syringes and lyosyringes) for administering one or more formulations described herein. In various embodiments, the kit can comprise formulation components for parenteral, subcutaneous, intramuscular or IV administration, sealed in a vial under partial vacuum in a form ready for loading into a syringe and administration to a subject. In this regard, the composition can be disposed therein under partial vacuum. In all of these embodiments and others, the kits can contain one or more vials in accordance with any of the foregoing, wherein each vial contains a single unit dose for administration to a subject.

The kits can comprise lyophilates, disposed as herein, that upon reconstitution provide compositions in accordance therewith. In various embodiment the kits can contain a lyophilate and a sterile diluent for reconstituting the lyophilate.

Also described herein, are methods for treating a subject in need of therapy, comprising administering to the subject an effective amount of a formulation as described herein. The therapeutically effective amount or dose of a formulation will depend on the disease or condition of the subject and actual clinical setting.

In an embodiment, a formulation as described herein can be administered by any suitable route, specifically by parental (including subcutaneous, intramuscular, intravenous and intradermal) administration. It will also be appreciated that the preferred route will vary with the condition and age of the recipient, and the disease being treated. Methods of determining the most effective means and dosage of administration are known to those of skill in the art and will vary, without limitation, with the composition used for therapy, the purpose of the therapy, and the subject being treated. Single or multiple administrations can be carried out, without limitation, the dose level and pattern being selected by the treating physician. Suitable dosage formulations and methods of administering the agents are known in the art.

The formulations as described herein can be used in the manufacture of medicaments and for the treatment of humans and other animals by administration in accordance with conventional procedures.

Also provided herein are combinatorial methods for developing suitable virus formulations using combinations of amino acids. These methods are effective for developing stable liquid or lyophilized formulations, and particularly pharmaceutical virus formulations.

Compositions in accordance with embodiments described herein have desirable properties, such as desirable solubility, viscosity, syringeability and stability. Lyophilates in accordance with embodiments described herein have desirable properties, as well, such as desirable recovery, stability and reconstitution.

In an embodiment, the pH of the pharmaceutical formulation is at least about 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, or 9.

In an embodiment, the pH of the pharmaceutical formulation is from about 3 to about 9, about 4 to about 19, about 5 to about 9, about 6 to about 8, about 6 to about 7, about 6 to about 9, about 5 to about 6, about 5 to about 7, about 5 to about 8, about 4 to about 9, about 4 to about 8, about 4 to about 7, about 4 to about 6, about 4 to about 5, about 3 to about 8, about 3 to about 7, about 3 to about 6, about 3 to about 5, about 3 to about 4, about 7 to about 8, about 7 to about 9, about 7 to about 10.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. A method of preventing or treating a Covid-19 infection by blocking interaction with a host cell in a subject, the method comprising administering a therapeutic amount of a peptide of SEQ ID NO:1 to the subject, wherein the peptide is administered as a nasal spray or inhalant.

2. The method of claim 1, wherein the peptide prevents or attenuates formation of a complex between a viral surface protein and a receptor on a host cell, wherein the viral surface protein is a S-glycoprotein.

3. The method of claim 1, wherein the peptide comprises a carboxy-terminal lysine residue and a biotin residue.

4. The method of claim 1, wherein the peptide is comprised of at least one of a lysine residue, a biotin residue, a thienoimidazole derivative and a FITC.

5. A method of preventing or treating a coronavirus virus infection in a patient, the method comprising administering a therapeutic amount of a peptide of SEQ ID NO: 1 to the patient, wherein the peptide comprises a carboxy-terminal lysine residue and a biotin residue.

* * * * *